(12) United States Patent
Richardson et al.

(10) Patent No.: US 9,861,691 B2
(45) Date of Patent: Jan. 9, 2018

(54) NOROVIRUS VACCINE FORMULATIONS

(71) Applicant: TAKEDA VACCINES, INC., Bozeman, MT (US)

(72) Inventors: Charles Richardson, Bozeman, MT (US); Thomas S. Vedvick, Federal Way, WA (US); Thomas R. Foubert, Bozeman, MT (US); William T. Tino, Belgrade, MT (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 14/796,714

(22) Filed: Jul. 10, 2015

(65) Prior Publication Data

US 2016/0008455 A1    Jan. 14, 2016

Related U.S. Application Data

(63) Continuation of application No. 13/837,885, filed on Mar. 15, 2013, now Pat. No. 9,272,028, which is a continuation of application No. 13/330,854, filed on Dec. 20, 2011, now abandoned, which is a continuation of application No. 12/816,495, filed on Jun. 16, 2010, now Pat. No. 8,431,116, which is a continuation of application No. 12/093,921, filed as application No. PCT/US2007/079929 on Sep. 28, 2007, now Pat. No. 7,955,603.

(60) Provisional application No. 60/973,392, filed on Sep. 18, 2007, provisional application No. 60/847,912, filed on Sep. 29, 2006.

(51) Int. Cl.

| *A61K 39/12* | (2006.01) |
|---|---|
| *A61K 39/125* | (2006.01) |
| *C07K 16/10* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/12* (2013.01); *A61K 39/125* (2013.01); *A61K 39/39* (2013.01); *C07K 16/10* (2013.01); *C12N 7/00* (2013.01); A61K 2039/5258 (2013.01); A61K 2039/54 (2013.01); A61K 2039/543 (2013.01); A61K 2039/55572 (2013.01); A61K 2039/70 (2013.01); C12N 2770/16023 (2013.01); C12N 2770/16034 (2013.01)

(58) Field of Classification Search
CPC .... A61K 2039/543; A61K 2039/55572; A61K 2039/5258; A61K 39/12; A61K 2039/70; A61K 47/36; A61K 9/1652; A61K 9/0034; A61K 9/006; A61K 39/00; A61K 2039/5555; A61K 39/295; C12N 2770/16034; C12N 2770/16023; C12N 2740/16034; C12N 2760/16134; C12N 2760/18534; C12N 2770/20034; C12N 2720/12323; C12N 2730/10123; C07K 16/10; C07K 14/08; C07K 14/4727; G01N 2333/08

See application file for complete search history.

(56) References Cited

U.S. PATENT DOCUMENTS

| 5,645,051 | A | 7/1997 | Schultz et al. |
|---|---|---|---|
| 5,861,241 | A | 1/1999 | Herrmann et al. |
| 5,953,727 | A | 9/1999 | Maslyn et al. |
| 6,165,502 | A | 12/2000 | Oleske et al. |
| 6,251,678 | B1 | 6/2001 | Volkin et al. |
| 6,391,318 | B1 | 5/2002 | Illum et al. |
| 6,491,919 | B2 | 12/2002 | Crane |
| 6,572,862 | B1 | 6/2003 | Estes et al. |
| 6,602,697 | B1 | 8/2003 | Cook, III |
| 6,942,865 | B2 | 9/2005 | Estes et al. |
| 7,067,638 | B1 | 6/2006 | Takeda et al. |
| 7,481,997 | B1 | 1/2009 | Hardy |
| 7,527,801 | B2 * | 5/2009 | Coit ...................... A61K 39/12 424/184.1 |
| 7,955,603 | B2 * | 6/2011 | Richardson .......... A61K 39/125 424/204.1 |
| 8,119,145 | B2 | 2/2012 | Coit et al. |
| 8,124,104 | B2 | 2/2012 | Coit et al. |
| 8,142,793 | B2 | 3/2012 | Coit et al. |
| 8,431,116 | B2 * | 4/2013 | Richardson .......... A61K 39/125 424/682 |
| 8,841,120 | B2 * | 9/2014 | Richardson ............ A61K 39/12 435/320.1 |

(Continued)

FOREIGN PATENT DOCUMENTS

| EP | 1186890 A1 | 3/2002 |
|---|---|---|
| EP | 2360175 A2 | 8/2011 |
| JP | 10-500847 A | 1/1998 |
| JP | 2002-508748 A | 3/2002 |
| JP | 2002-536340 A | 10/2002 |
| JP | 2005-200420 A | 7/2005 |
| JP | 2005-524674 A | 8/2005 |
| JP | 2005-525415 A | 8/2005 |
| JP | 2005-538939 A | 12/2005 |
| JP | 2006-502979 A | 1/2006 |

(Continued)

OTHER PUBLICATIONS

Tacket et al. Clinical Immunology vol. 108, Issue 3, Sep. 2003, pp. 241-247.*

(Continued)

*Primary Examiner* — Bao Li
(74) *Attorney, Agent, or Firm* — Cooley LLP

(57) ABSTRACT

The present invention relates to antigenic and vaccine compositions comprising Norovirus antigens and adjuvants, in particular, mixtures of monovalent VLPs and mixtures of multivalent VLPs, and to a process for the production of both monovalent and multivalent VLPs, the VLPs comprising capsid proteins from one or more Norovirus genogroups.

18 Claims, 19 Drawing Sheets

(56) References Cited

U.S. PATENT DOCUMENTS

| | | | |
|---|---|---|---|
| 8,980,275 B2 | 3/2015 | Steadman et al. | |
| 9,272,028 B2* | 3/2016 | Richardson | A61K 39/125 |
| 9,308,249 B2* | 4/2016 | Richardson | A61K 39/125 |
| 9,518,096 B2 | 12/2016 | Richardson et al. | |
| 2004/0063188 A1 | 4/2004 | Robinson et al. | |
| 2004/0265377 A1 | 12/2004 | Seager | |
| 2005/0152911 A1 | 7/2005 | Hardy | |
| 2005/0154053 A1 | 7/2005 | Rhijn et al. | |
| 2005/0155113 A1 | 7/2005 | Hamilton et al. | |
| 2005/0215501 A1 | 9/2005 | Lipford et al. | |
| 2005/0260225 A1 | 11/2005 | Goldberg et al. | |
| 2007/0207526 A1* | 9/2007 | Coit | A61K 39/12 435/91.1 |
| 2008/0299152 A1 | 12/2008 | Richardson et al. | |
| 2010/0150961 A1 | 6/2010 | Vedvick et al. | |
| 2010/0266636 A1 | 10/2010 | Richardson et al. | |
| 2011/0070260 A1 | 3/2011 | Baric et al. | |
| 2011/0182975 A1 | 7/2011 | Richardson et al. | |
| 2011/0195113 A1 | 8/2011 | Richardson et al. | |
| 2012/0093861 A1 | 4/2012 | Richardson et al. | |
| 2012/0156243 A1 | 6/2012 | Richardson et al. | |
| 2013/0273102 A1 | 10/2013 | Richardson et al. | |
| 2013/0273105 A1 | 10/2013 | Richardson et al. | |
| 2013/0273147 A1 | 10/2013 | Richardson et al. | |
| 2013/0273148 A1 | 10/2013 | Richardson et al. | |
| 2014/0286994 A1 | 9/2014 | Richardson et al. | |
| 2015/0023995 A1 | 1/2015 | Richardson et al. | |
| 2016/0000899 A1 | 1/2016 | Richardson et al. | |

FOREIGN PATENT DOCUMENTS

| | | |
|---|---|---|
| JP | 2006-507800 A | 3/2006 |
| JP | 2006-516638 A | 7/2006 |
| JP | 2006-518748 A | 8/2006 |
| JP | 2007-145775 A | 6/2007 |
| JP | 2007-537137 A | 12/2007 |
| JP | 2008-511556 A | 4/2008 |
| JP | 2009-516529 A | 4/2009 |
| JP | 2010-505766 A | 2/2010 |
| JP | 2011-506264 A | 3/2011 |
| JP | 5476544 B | 2/2014 |
| WO | WO 92/16543 A1 | 10/1992 |
| WO | WO 93/21325 A1 | 10/1993 |
| WO | WO 1998/050071 A1 | 11/1998 |
| WO | WO 2000/079280 A1 | 12/2000 |
| WO | WO 2003/077942 A2 | 9/2003 |
| WO | WO 2003/078455 A2 | 9/2003 |
| WO | WO 2005/020889 A2 | 3/2005 |
| WO | WO 2005/030806 A2 | 4/2005 |
| WO | WO 2005/060966 A1 | 7/2005 |
| WO | WO 2006/044857 A2 | 4/2006 |
| WO | WO 2006/067632 A2 | 6/2006 |
| WO | WO 2006/086188 A2 | 8/2006 |
| WO | WO 2006/091517 A2 | 8/2006 |
| WO | WO 2006/097530 A2 | 9/2006 |
| WO | WO 2006/136566 A1 | 12/2006 |
| WO | WO 2007/053188 A2 | 5/2007 |
| WO | WO 2007/081447 A1 | 7/2007 |
| WO | WO 2007/081447 A2 | 7/2007 |
| WO | WO 2008/042789 A1 | 4/2008 |
| WO | WO 2010/017542 A1 | 8/2008 |
| WO | WO 2009/039229 A2 | 3/2009 |
| WO | WO 2013/009849 A1 | 1/2013 |

OTHER PUBLICATIONS

Baldridge et al., "Taking a Toll on human disease: Toll-like receptor 4 agonists as vaccine adjuvants and monotherapeutic agents," Exp. Opin. Biol. Ther. 4(7):1129-1138 (2004).

Bok et al., "Chimpanzees as an animal model for human norovirus infection and vaccine development," Proc. Natl. Acad. Sci. USA 108(1):325-330 (2011).

Broadbent and Subbarao, "Influenza virus vaccines: lessons from the 2009 H1N1 pandemic," Curr. Opin. Virol. 1:254-232 (2011).

Cuellar et al., "Size and mechanical stability of norovirus capsids depend on pH: a nanoindetation study," J. Gen. Virol. 91:2449-2456 (2010).

Da Silva et al., "Adsorption and Aggregation Properties of Norovirus GI and GII Virus-like Particles Demonstrate Differing Responses to Solution Chemistry," Environ. Sci. Technol. 45(2):520-526 (2011).

Dagan et al., "Reduced Response to Multiple Vaccines Sharing Common Protein Epitopes That Are Administered Simultaneously to Infants," Infect. Immun. 66(5):2093-2098 (1998).

European Search Report, EP appl. No. 13157572.2, 9 pages (dated Jul. 23, 2013).

European Search Report, EP appl. No. 13157573.0, 6 pages (dated Apr. 5, 2013).

European Search Report, EP appl. No. 13173005.3, 5 pages (dated Jul. 16, 2013).

Frey et al., "Interference of Antibody Production to Hepatitis B Surface Antigen in a Combination Hepatitis A/Hepatitis B Vaccine," J. Infect. Dis. 180:2018-2022 (1999).

Giannini et al., "Enhanced humoral and memory B cellular immunity using HPV16/18 L1 VLP vaccine formulated with the MPL/ aluminium salt combination (AS04) compared to aluminium salt only," Vaccine 24:5937-5949 (2006).

Guy et al., "Evaluation of Interferences between Dengue Vaccine Serotypes in a Monkey Model," Am. J. Trop. Med. Hyg. 80(2):302-311 (2009).

Hardy, Michele E., "Norovirus protein structure and function", FEMS Microbiology (2005); 253: 1-8.

Kawana et al., "A surface immunodeterminant of human papillomavirus type 16 minor capsid protein L2." Virology (1998); 245.2: 353-359.

Larke et al., "Combined single-clade candidate HIV-1 vaccines induce T cell responses limited multiple forms of in vivo immune interference," Eur. J. Immunol. 37:566-577 (2007).

Lew et al., "Molecular Characterization and Expression of the Capsid Protein of a Norwalk-like Virus Recovered from a Desert Shield Troop with Gastroenteritis," Virol. 319-325 (1994).

Martin et al., "Role of Innate Immune Factors in the Adjubant Activity of Monophosphoryl Lipid A," Infect. Immun. 71(5):2498-2507 (2003).

Parra and Green, "Sequential Gastroenteritis Episodes Caused by 2 Norovirus Genotypes," Emerg. Infect. Dis. 20(6):1016-1018 (2014).

Pastrana et al., "Cross-neutralization of cutaneous and mucosal Papillomavirus types with anti-sera to the amino terminus of L2." Virology (2005); 337.2: 365-372.

Reagan-Shaw et al., "Dose translation from animal to human studies revisited," FASEB J. 22:659-661(2007).

Richardson et al., "Norovirus virus-like particle vaccines for the prevention of acute gastroenteritis," Expert Rev. Vaccines 12(2):155-167 (2013).

Supplementary European Search Report, EP appl. No. 12811916.1, 8 pages (dated Feb. 20, 2015).

Zhang et al., "Trivalent Human Papillomavirus (HPV) VLP vaccine covering HPV type 58 can elicit high level of humoral immunity but also induce immune interference among component types," Vaccine 28:3479-3487 (2010).

Zheng et al., "Norovirus classification and proposed strain nomenclature," Virology 346:312-323 (2006).

Chachu, Karen A., et al. "Immune mechanisms responsible for vaccination against and clearance of mucosal and lymphatic norovirus infection." PLoS Pathog (2008); 4.12: e1000236, 13 pages.

Glass, R.I., et al. "Norovirus gastroenteritis." New England Journal of Medicine (2009); 361.18: 1776-1785.

Lin, S.W., et al. "Intramuscular rather than oral administration of replication-defective adenoviral vaccine vector induces specific CD8+ T-cell responses in the gut." Vaccine (2007); 25(12): 2187-2193.

Liu, Guangliang, et al. "Primary high-dose murine norovirus 1 infection fails to protect from secondary challenge with homologous virus." Journal of Virology (2009); 83.13: 6963-6968.

(56) References Cited

OTHER PUBLICATIONS

Oliver, S. L., et al. "Genotype 1 and genotype 2 bovine noroviruses are antigenically distinct but share a cross-reactive epitope with human noroviruses." Journal of Clinical Microbiology (2006); 44.3: 992-998.
Song, Wei, et al., "Research Progress on Molecular Biology Feature of Noroviruses and its Subunit Vaccine." Journal of Agricultural Science and Technology (2010); 12(6): 43-48.
U.S. Appl. No. 12/678,813 (pending).
U.S. Appl. No. 12/765,641 (abandoned).
U.S. Appl. No. 13/330,854 (abandoned).
U.S. Appl. No. 13/836,446 (pending).
U.S. Appl. No. 13/837,389 (pending).
U.S. Appl. No. 13/840,403 (pending).
U.S. Appl. No. 14/796,614 (pending).
MMWR, 2011, Updated Norovirus Outbreak Management and Disease Prevention Guidelines, 20 pages. [https://www.cdc.gov/mmwr/preview/mmwrhtml/rr6003a1.htm] downloaded May 1, 2017.
Allen et al., "Analysis of Amino Acid Variation in the P2 Domain of the GII-4 Norovirus VP1 Protein Reveals Putative Variant-Specific Epitopes," PLOS One, vol. 3: e1485, 2008.
Ando et al., "Genetic Classification of 'Norwalk-like Viruses,'" The Journal of Infectious Diseases, vol. 181(Suppl 2): S336-S348, 2000.
Angioni, C.F., "Supplementary European Search Report," 9 pages, from European Patent Appl. No. 07853688.5, European Patent Office, The Hague, Netherlands (dated Sep. 22, 2010).
Ausar et al., "Conformational stability and disassembly of norwalk virus like particles: effect of pH and temperature,"J. Biol. Chem., vol. 281: 19478-19488, 2006.
Baldrick et al., Safety evaluation of monophosphoryl lipid A (MPL): an immunostimulatory adjuvant. Regulatory Toxicology and Pharmacology 2002; vol. 35:398-413.
Baldridge et al., Monophosphoryl lipid A enhances mucosal and systemic immunity to vaccine antigens following intranasal administration. Vaccine 2000; vol. 18:2416-2425.
Ball et al., Oral Immunization with Recombinant Norwalk Virus-Like Particles Induces a Systemic and Mucosal Immune Response in Mice. Journal of Virology 1998; vol. 72(2): 1345-1353.
Ball et al., Recombinant Norwalk virus-like particles given orally to volunteers: phase I study. Gastroenterology 1999; vol. 117:40-48.
Baric et al., "Expression and Self-Assembly of Norwalk Virus Capsid Protein from Venezuelan Equine Encephalitis Virus Replicons," J. Virol. 76(6):3023-3030 (2002).
Bertolotti-Ciarlet et al., "Structural Requirements for the Assembly of Norwalk Virus-Like Particles," J. Virol. 76(8):4044-4055 (2002).
Bull et al., "Emergence of a New Norovirus Genotype II.4 Variant Associated with Global Outbreaks of Gastroenteritis," Journal of Clinical Microbiology, vol. 44: 327-333, 2006.
Cachia et al., "The use of synthetic peptides in the design of a consensus sequence vaccine for Pseudomonas aeruginosa," J. Pept. Res. 52(4):289-299 (1998).
Cao et al., "Structural Basis for the Recognition of Blood Group Trisaccharides by Norovirus," J. Virol. 81(11):5949-5957 (2007).
Carpenter et al., Rational design of stable lyophilized protein formulations: some practical advice, Pharmaceutical Research, vol. 14: 969-975, 1997.
Cheetham et al., "Binding patterns of human norovims-like particles to buccal and intestinal tissues of gnotobiotic pigs in relation to A/H histo-blood group antigen expression," Journal of Virology, vol. 81: 3535-3544, 2007.
Chen et al., "X-ray structure of a native calicivirus: Structural insights into antigenic diversity and host specificity," Proc. Natl Acad. Sci. USA 103(21):8048-8053 (2006).
Childers et al., "Adjuvant activity of monophosphoryl lipid A for nasal and oral immunization with soluble or liposome-associated antigen," Infection and Immunity, vol. 68: 5509-5516, 2000.
Davis and Illum, Absorption enhancers for nasal drug delivery. Clinical Pharmacokinetics 2003; vol. 42:1107-1128.

Estes et al., Norwalk Virus Vaccines: Challenges and Progress. The Journal of Infectious Disease 2000; vol. 181(Suppl 2): S367-373.
Fankhauser et al., "Molecular Epidemiology of "Norwalk-like viruses" in Outbreaks of Gastroenteritis in the United States," J. Infect. Dis. 178(6):1571-1578 (1998).
Foubert et al., "Preclinical Development of a Broad Spectrum Norovirus Vaccine," AAPS National Biotechnology Conference, http://abstracts.aapspharmaceutica.com/ExpoNBC09/CC/forms/attendee/index.aspx?content=sessionInfo&sessionId=150 (2009).
Gray et al., Detection of immunoglobulin M (IgM), IgA, and IgG Norwalk virus-specific antibodies by indirect enzyme-linked immunosorbent assay with baculovirus-expressed Norwalk virus capsid antigen in adult volunteers challenged with Norwalk virus. Journal of Clinical Microbiology 1994; vol. 32:3059-3063.
Guerrero et al., Recombinant Norwalk Virus-Like Particles Administered Intranasally to Mice Induce Systemic and Mucosal (Fecal and Vaginal) Immune Responses. Journal of Virology 2001; vol. 75:9713-9722.
Han et al., Immune responses to bovine norovirus-like particles with various adjuvants and analysis of protection in gnotobiotic calves. Vaccine 2006; vol. 24:317-326.
Han et al., "Thermosensitive and mucoadhesive delivery systems of mucosal vaccines," Methods, vol. 38:106-111, 2006.
Hansman et al., Genetic and antigenic diversity among Noroviruses. Journal of General Virology 2006; vol. 87: 909-919.
Harrington et al., "Systemic, Mucosal, and Heterotypic Immune Induction in Mice Inoculated with Venezuelan Equine Encephalitis Replicons Expressing Norwalk Virus-Like Particles," J. Virol. 76(2):730-742 (2002).
Herbst-Kralovetz et al., "Norwalk virus-like particles as vaccines," Exp. Rev. Vaccines 9(3):299-307 (2010).
Huang et al., "Noroviruses Bind to Human ABO, Lewis, and Secretor Histo-Blood Group Antigens: Identification of 4 Distinct Strain-Specific Patterns," J. Infect. Dis. 188(1):19-31 (2003).
Hutson et al., Norovirus disease: changing epidemiology and host susceptibility factors. TRENDS in Microbiology 2004; vol. 12(6):279-287.
Hutson et al., "Norwalk Virus-Like Particle Hemagglutination by Binding to H Histo-Blood Group Antigens," J. Virol. 77(1):405-415 (2003).
Illum et al., Chitosan as a novel nasal delivery system for peptide drugs. Pharmaceutical Research 1994.; vol. 11:1186-1189.
Illum et al., Chitosan as a novel nasal delivery system for vaccines. Advanced Drug Delivery Reviews 2001; vol. 51:81-96.
Illum et al., Nasal drug delivery—possibilities, problems and solutions. Journal of Controlled Release 2003; vol. 87:187-198.
International Search Report, 2 pages, PCT appl. No. PCT/US2007/079929 (dated Mar. 11, 2008).
International Search Report, 3 pages, PCT appl. No. PCT/US2008/076763 (dated Jul. 15, 2009).
International Search Report, 3 pages, PCT appl. No. PCT/US2009/053249 (dated Dec. 14, 2009).
International Search Report, 3 pages, PCT appl. No. PCT/US2012/046222 (dated Oct. 2, 2012).
Jaimes et al., "Maturation and Trafficking Markers on Rotavirus-Specific B Cells during Acute Infection and Convalescence in Children," J. Virol 78:10967-10976 (2004).
Jiang et al., "Expression, Self-Assembly, and Antigenicity of the Norwalk Virus Capsid Protein," J. Virol. 66(11):6527-6532 (1992).
Jiang et al., "Norwalk virus genome cloning and characterization," Science 250:1580-1583 (1990).
Johnson et al., Multiple Challenge Study of Host Susceptibility to Norwalk Gastroenteritis in U.S. Adults. The Journal of Infectious Disease 1990; vol. 161: 18-21.
Kamata et al., "Increased Frequency of Surface IgA-Positive Plasma Cells in the Intestinal Lamina Propia and Decreased IgA Excretion in Hyper IgA (HIGA) Mice, a Murine Model of IgA Nephropathy with Hyperscrum IgA," J. Immunol. 165:1387-1394 (2000).
Ligocyte Pharmaceuticals, "Ligocyte Pharmaceuticals initiates U.S. clinical trial of norovirus vaccine," http://www.ligocyte.com/news/documents/LIGOCYTE-PHARMACEUTICALS-4-3-2007.pdf, Apr. 3, 2007, 2 pages.

(56) References Cited

OTHER PUBLICATIONS

Lindell et al., "Molecular Epidemiology of Norovirus Infections in Stockholm, Sweden, during the Years 2000 to 2003: Association of the GGIIb Genetic Cluster with Infection in Children," Journal of Clinical Microbiology, vol. 43: 1086-1092, 2005.

Lindesmith et al., Cellular and humoral immunity following Snow Mountain virus challenge. Journal of Virology 2005; vol. 79(5): 2900-2909.

Lindesmith et al., Human susceptibility and resistance to Norwalk infection. Nature Medicine 2003; vol. 9(5): 548-553.

Lindesmith et al., "Mechanisms of GII.4 Norovirus Persistence in Human Populations," PLOS One, vol. 5: e31, 2008.

Lobue et al., "Alphavirus adjuvanted norovirus-like particle vaccines: heterologous, humoral, and mucosal immune responses protect against murine norovims challenge," J. Virol., vol. 83(7): 3212-3227, 2009.

Lobue et al., Multivalent Norovirus vaccines induce strong mucosal and systemic blocking antibodies against multiple strains. Vaccine 2006; vol. 24(24): 5220-5234.

Malcolmson and Embleton, "Dry powder formulations for pulmonary delivery," Pharmaceutical Science and Technology Today, vol. 1:394-398, 1998.

Mason et al., "Expression of Norwalk virus capsid protein in transgenic tobacco and potato and its oral immunogenicity in mice," Proc. Natl Acad. Sci. USA 93(11):5335-5340 (1996).

Matsui et al., Immunity to Calicivirus infection. The Journal of Infectious Diseases 2000; vol. 181(S2): S331-335.

McBurney et al., "Developing Broadly Reactive HIV-1/AIDS Vaccines: A Review of Polyvalent and Centralized HIV-1 Vaccines," Curr. Pharm. Design 13(19):1957-1964 (2007).

Mead et al., Food Related Illness and Death in the U.S., Emerging Infectious Diseases 1999; vol. 5(5): 607-635.

Muthumani et al., "Immunogenicity of novel consensus-based DNA vaccines against Chikungunya virus," Vaccine 26(40):5128-5134 (2008).

Nicollier-Jamot et al., Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. Vaccine 2004; vol. 22:1079-1086.

Noel et al., Correlation of patient immune responses with genetically characterized small round-structured viruses involved in outbreaks of nonbacterial acute gastroenteritis in the United States, 1990 to 1995. Journal of Medical Virology 1997; vol. 53:372-383.

O'Hagan et al., "Recent developments in adjuvants for vaccines against infectious diseases," Biomol. Eng. 18(3):69-85 (2001).

Parrino et al., Clinical immunity in acute gastroenteritis caused by Norwalk agent. New England Journal of Medicine 1977; vol. 297:86-89.

Partial European Searcht Report, 7 pages, EP appl. No. 13157572.2 (dated Apr. 5, 2013).

Pelosi et al., "The Seroepidemiology of Genogroup 1 and Genogroup 2 Norwalk-Like Viruses in Italy," J. Med. Virol. 58:93-99 (1999).

Periwal et al., A Modified Cholera Holotoxin CT-E29H Enhances Systemic and Mucosal Immune Responses to Recombinant Norwalk Virus-like Particle Vaccine. Vaccine 2003; vol. 21:376-385.

Prasad et al., "Structural studies of recombinant norwalk capsids," J. Infect. Dis., vol. 181(s2), S317-S321, 2000.

Rasmussen et al., "In Multiple Myeloma Clonotypic $CD38^-/CD19^+/CD27^+$ Memory B Cells Recirculate Through Bone Marrow, Peripheral Blood and Lymph Nodes," Leuk. Lymph. 45(7):1413-1417 (2004).

Richardson et al., "Norovirus Vaccine Formulations," U.S. Appl. No. 12/816,495, filed Jun. 16, 2010.

Sha et al., "Activation of Airway Epithelial Cells by Toll-Like Receptor Agonists," Am. J. Respir. Cell Mol. Biol. 31(3):358-364 (2004).

Siebenga et al., "Epochal Evolution of GGII.4 Norovirus Capsid Proteins from 1995 to 2006," Journal of Virology, vol. 81: 9932-9941, 2007.

Singh et al., "A preliminary evaluation of alternative adjuvants to alum using a range of established and new generation vaccine antigens," Vaccine 24(10):1680-1686 (2006).

Souza et al., "A human norovirus-like particle adjuvanted with ISCOM or mLT induces cytokine and antibody responses and protection to the homologous GII.4 human norovirus in a gnotobiotic pig disease model," Vaccine, vol. 25: 8448-8459, 2007.

Supplementary European Search Report, 13 pages, EP appl. No. 08832560.0 (dated Apr. 5, 2012).

Supplementary European Search Report, 8 pages, EP appl. No. 09805653.4 (dated Dec. 2, 2011).

Tacket et al., Humoral, mucosal, and cellular immune response to oral Norwalk virus-like particles in volunteers. Clinical Immunology 2003; vol. 108: 241-247.

Tacket et al., "Human immune responses to a novel norwalk virus vaccine delivered in transgenic potatoes.," J. Infect. Dis., vol. 182(1): 302 305, 2000.

Ugwoke et al., "Nasal mucoadhesive drug delivery: Background, applications, trends and future perspectives," Advanced Drug Delivery Reviews, vol. 57: 1640-1665, 2005.

Wang et al., "Effective synthetic peptide vaccine for foot-and-mouth disease in swine," Vaccine 20(19-20):2603-2610 (2002).

Written Opinion of the International Searching Authority, 4 pages, PCT appl. No. PCT/US2007/079929 (dated Mar. 11, 2008).

Written Opinion of the International Searching Authority, 5 pages, PCT appl. No. PCT/US2008/076763 (dated Jul. 15, 2009).

Written Opinion of the International Searching Authority, 7 pages, PCT appl. No. PCT/US2009/053249 (dated Dec. 14, 2009).

Written Opinion of the International Searching Authority, 6 pages, PCT appl. No. PCT/US2012/046222 (dated Oct. 2, 2012).

Wyatt et al., Comparison of three agents of acute infectious nonbacterial gastroenteritis by cross-challenge in volunteers. Journal of Infecious. Diseases 1974.; vol. 129:709-714.

Xia et al., "Norovirus Capsid Protein Expressed in Yeast Forms Virus-like Particles and Stimulates Systemic and Mucosal Immunity in Mice Following an Oral Administration of Raw Yeat Extracts," J. Med Virol. 79:74-83 (2007).

Clark and Offit, "Vaccines for rotavirus gastroenteritis universally needed for infants." Pediatric Annals (2004); 33(8): 537-543.

Kitamoto et al., "Cross-Reactivity among Several Recombinant Calicivirus Virus-Like Particles (VLPs) with Monoclonal Antibodies Obtained from Mice Immunized Orally with One Type of VLP." J. Clin. Microbiol. (2002); 40(7): 2459-2465.

Midthun and Kapikian. "Rotavirus vaccines: an overview." Clinical Microbiology Reviews (1996); 9(3): 423-434.

Nakata, S., "Vaccine development for Norwalk Virus." Nippon Rinsho (2002); 60(6): 1222-1227 (with English Abstract and English translation), 12 pages.

Notice of Opposition in European Patent No. EP 2601970 (Application No. EP 13157573.0), filed Jul. 21, 2017, 40 pages.

Ball et al., "Recombinant Norwalk virus-like particles as an oral vaccine." Archives of Virology (1996); 12: 243-249.

* cited by examiner

A

B

NOROVIRUS VACCINE FORMULATIONS

CROSS REFERENCE TO RELATED APPLICATIONS

This application is a continuation of U.S. patent application Ser. No. 13/837,885, filed Mar. 15, 2013, which is a continuation of U.S. patent application Ser. No. 13/330,854, filed Dec. 20, 2011, which is a continuation of U.S. patent application Ser. No. 12/816,495, filed Jul. 16, 2010, which issued as U.S. Pat. No. 8,431,116 on Apr. 30, 2013 and which is a continuation of U.S. patent application Ser. No. 12/093,921, filed May 15, 2008, which issued as U.S. Pat. No. 7,955,603 on Jun. 7, 2011 and which is a national stage application of International Application No. PCT/US2007/079929, filed Sep. 28, 2007, which claims priority to U.S. Patent Application Ser. No. 60/847,912, filed Sep. 29, 2006, and U.S. Patent Application Ser. No. 60/973,392, filed Sep. 18, 2007, all of which are herein incorporated by reference in their entireties.

STATEMENT OF GOVERNMENT SUPPORT

This invention was made with Government support under DAMD17-01-C-0400 and W81XWH-05-C-0135 awarded by the U.S. Army. The Government has certain rights in this invention.

FIELD OF THE INVENTION

The invention is in the field of vaccines, particularly vaccines for Noroviruses. In addition, the invention relates to methods of preparing vaccine compositions and methods of inducing an immunogenic response.

BACKGROUND OF THE INVENTION

Noroviruses are non-cultivatable human Caliciviruses that have emerged as the single most important cause of epidemic outbreaks of nonbacterial gastroenteritis (Glass et al., 2000; Hardy et al., 1999). The clinical significance of Noroviruses was under-appreciated prior to the development of sensitive molecular diagnostic assays. The cloning of the prototype genogroup I Norwalk virus (NV) genome and the production of virus-like particles (VLPs) from a recombinant Baculovirus expression system led to the development of assays that revealed widespread Norovirus infections (Jiang et al. 1990; 1992).

Noroviruses are single-stranded, positive sense RNA viruses that contain a non-segmented RNA genome. The viral genome encodes three open reading frames, of which the latter two specify the production of the major capsid protein and a minor structural protein, respectively (Glass et al. 2000). When expressed at high levels in eukaryotic expression systems, the capsid protein of NV, and certain other Noroviruses, self-assembles into VLPs that structurally mimic native Norovirus virions. When viewed by transmission electron microscopy, the VLPs are morphologically indistinguishable from infectious virions isolated from human stool samples.

Immune responses to Noroviruses are complex, and the correlates of protection are just now being elucidated. Human volunteer studies performed with native virus demonstrated that mucosally-derived memory immune responses provided short-term protection from infection and suggested that vaccine-mediated protection is feasible (Lindesmith et al. 2003; Parrino et al. 1997; Wyatt et al., 1974).

Although Norovirus cannot be cultivated in vitro, due to the availability of VLPs and their ability to be produced in large quantities, considerable progress has been made in defining the antigenic and structural topography of the Norovirus capsid. VLPs preserve the authentic confirmation of the viral capsid protein while lacking the infectious genetic material. Consequently, VLPs mimic the functional interactions of the virus with cellular receptors, thereby eliciting an appropriate host immune response while lacking the ability to reproduce or cause infection. In conjunction with the NIH, Baylor College of Medicine studied the humoral, mucosal and cellular immune responses to NV VLPs in human volunteers in an academic, investigator-sponsored Phase I clinical trial. Orally administered VLPs were safe and immunogenic in healthy adults (Ball et al. 1999; Tacket et al. 2003). At other academic centers, preclinical experiments in animal models have demonstrated enhancement of immune responses to VLPs when administered intranasally with bacterial exotoxin adjuvants (Guerrero et al. 2001; Nicollier-Jamot et al. 2004; Periwal et al. 2003). Collectively, these data suggest that a vaccine consisting of properly formulated VLPs represents a viable strategy to immunize against Norovirus infection.

SUMMARY OF THE INVENTION

The present invention provides antigenic and vaccine formulations comprising a Norovirus antigen. In one embodiment, the formulations further comprise at least one adjuvant. The Norovirus antigen can be derived from genogroup I or genogroup II viral sequences or a consensus viral sequence. The Norovirus formulations comprise antigenic peptides, proteins or virus-like particles (VLPs). In one embodiment, the VLPs may be denatured. In another embodiment, the antigenic peptides and proteins are selected from the group consisting of capsid monomers, capsid multimers, protein aggregates, and mixtures thereof. In another embodiment, the Norovirus antigen is present in a concentration from about 0.01% to about 80% by weight. The dosage of Norovirus antigen is present in an amount from about 1 μg to about 100 mg per dose.

In another embodiment, the Norovirus VLPs are recombinant VLPs produced in an expression system using a Norovirus nucleic acid sequence, which encodes at least one capsid protein or fragment thereof. The capsid protein is selected from the group consisting of VP1 and VP2 or a combination thereof. The expression system can be a recombinant cellular expression system such as a yeast, bacterial, insect, mammalian expression system, or a baculovirus-infected cellular expression system.

In still another embodiment, the composition further comprises a delivery agent, which functions to enhance antigen uptake by providing a depot effect, increase antigen retention time at the site of delivery, or enhance the immune response through relaxation of cellular tight junctions at the delivery site. The delivery agent can be a bioadhesive, preferably a mucoadhesive selected from the group consisting of glycosaminoglycans (e.g., chondroitin sulfate, dermatan sulfate chondroitin, keratan sulfate, heparin, heparan sulfate, hyaluronan), carbohydrate polymers (e.g., pectin, alginate, glycogen, amylase, amylopectin, cellulose, chitin, stachyose, unulin, dextrin, dextran), cross-linked derivatives of poly(acrylic acid), polyvinyl alcohol, polyvinyl pyrollidone, polysaccharides (including mucin and other mucopolysaccharides) cellulose derivatives (e.g., hydroxypropyl methylcellulose, carboxymethylcellulose), proteins (e.g. lectins, fimbrial proteins), and deoxyribonucleic acid. Preferably, the mucoadhesive is a polysaccharide. More preferably, the mucoadhesive is chitosan, or a mixture containing chitosan, such as a chitosan salt or chitosan base.

In yet another embodiment, the present invention provides a composition further comprising an adjuvant. The adjuvant may be selected from the group consisting of toll-like receptor (TLR) agonists, monophosphoryl lipid A (MPL®), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, endotoxins, for instance bacterial endotoxins and liposomes. Preferably, the adjuvant is a toll-like receptor (TLR) agonist. More preferably, the adjuvant is MPL®.

The compositions of the present invention may be provided as a liquid formulation or a dry powder formulation. Dry power formulations of the present invention may contain an average particle size from about 10 to about 500 micrometers in diameter. In one embodiment, the composition is an antigenic formulation. In another embodiment, the composition is formulated for administration as a vaccine. Suitable routes of administration include mucosal, intramuscular, intravenous, subcutaneous, intradermal, subdermal, or transdermal. In particular, the route of administration may be intramuscular or mucosal, with preferred routes of mucosal administration including intranasal, oral, or vaginal routes of administration. In another embodiment, the composition is formulated as a nasal spray, nasal drops, or dry powder, wherein the formulation is administered by rapid deposition within the nasal passage from a device containing the formulation held close to or inserted into the nasal passageway. In another embodiment, the formulation is administrated to one or both nostrils.

The present invention also provides methods for generating an immune response to Norovirus in a subject, comprising administering to the subject an antigenic formulation or a vaccine comprising the Norovirus composition. In one embodiment, the antigenic formulations and vaccines comprising the Norovirus composition find use in generating antibodies to one or more Norovirus antigens. In another embodiment, the Norovirus vaccine formulations may be used to treat Norovirus infections.

DETAILED DESCRIPTION OF THE INVENTION

Figure 1:
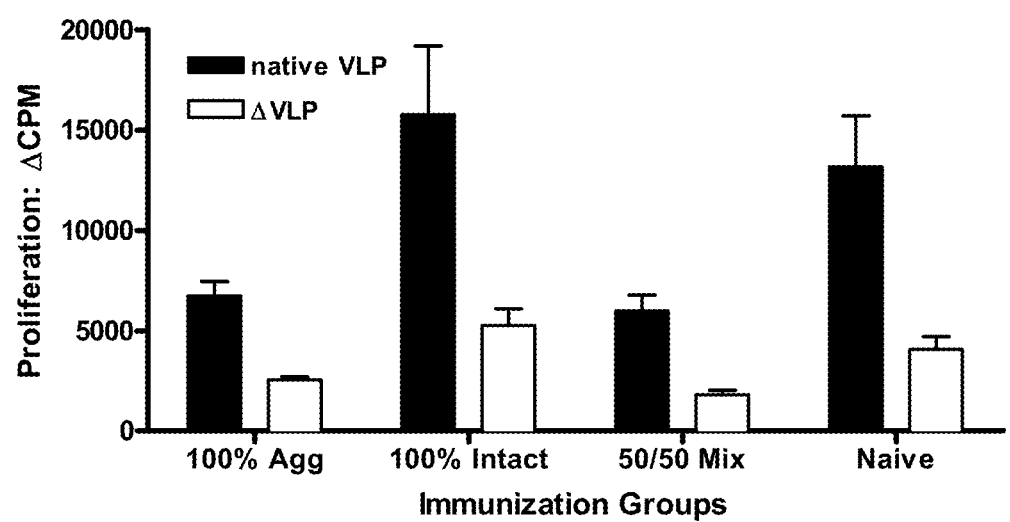
FIG. 1 illustrates an in vitro antigen-specific proliferation assay of murine cervical lymph node cells following in vivo intranasal immunization with 10 μg VLP.
Figure 2:
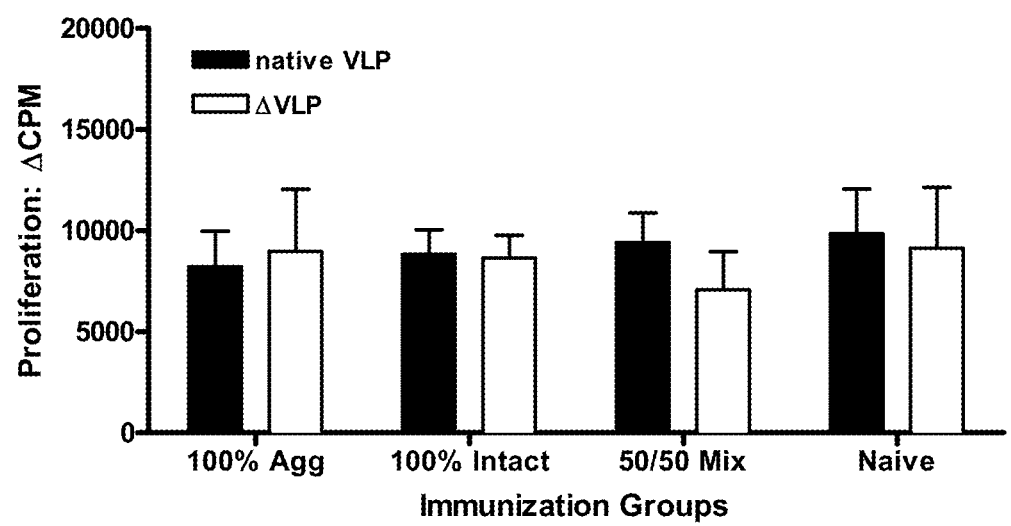
FIG. 2 illustrates in vitro antigen-specific proliferation assay of splenocytes following in vivo intranasal immunization with 10 μg VLP.
Figure 3:
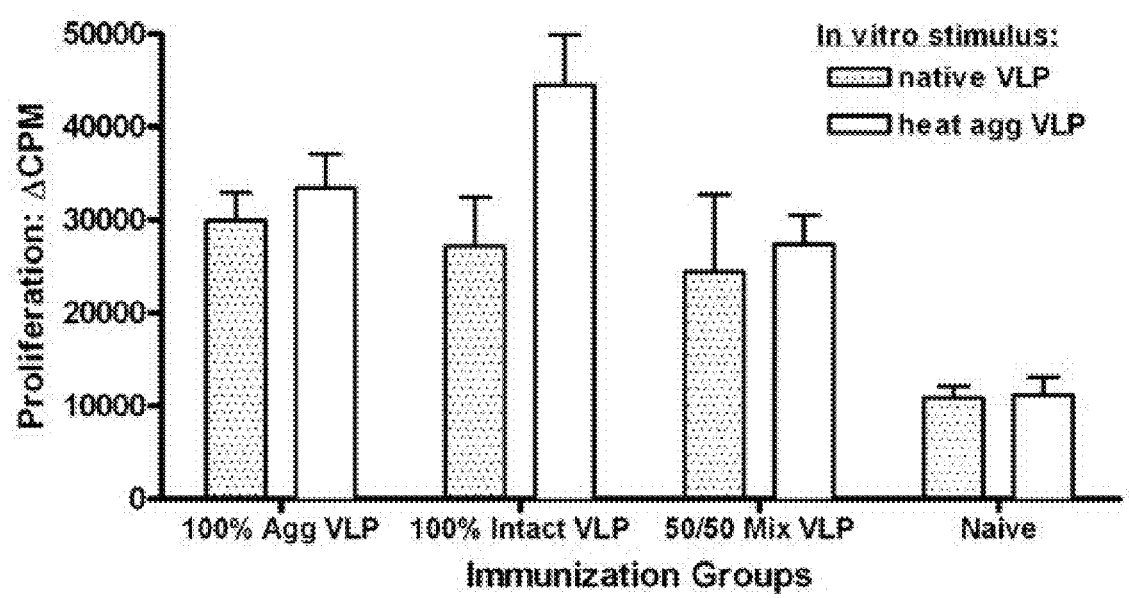
FIG. 3 illustrates in vitro antigen-specific proliferation assay of splenocytes following in vivo intraperitoneal immunization with 25 μg VLP.
Figure 4:
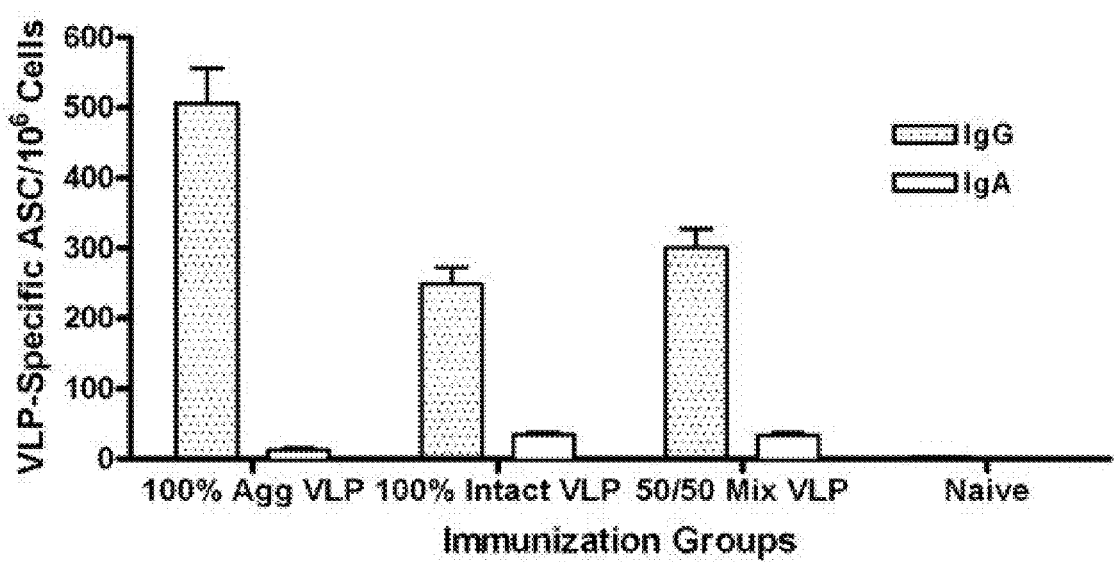
FIG. 4 illustrates VLP-specific IgG or IgA from antibody secreting cells (ASCs) measured by ELISPOT assay.
Figure 5:
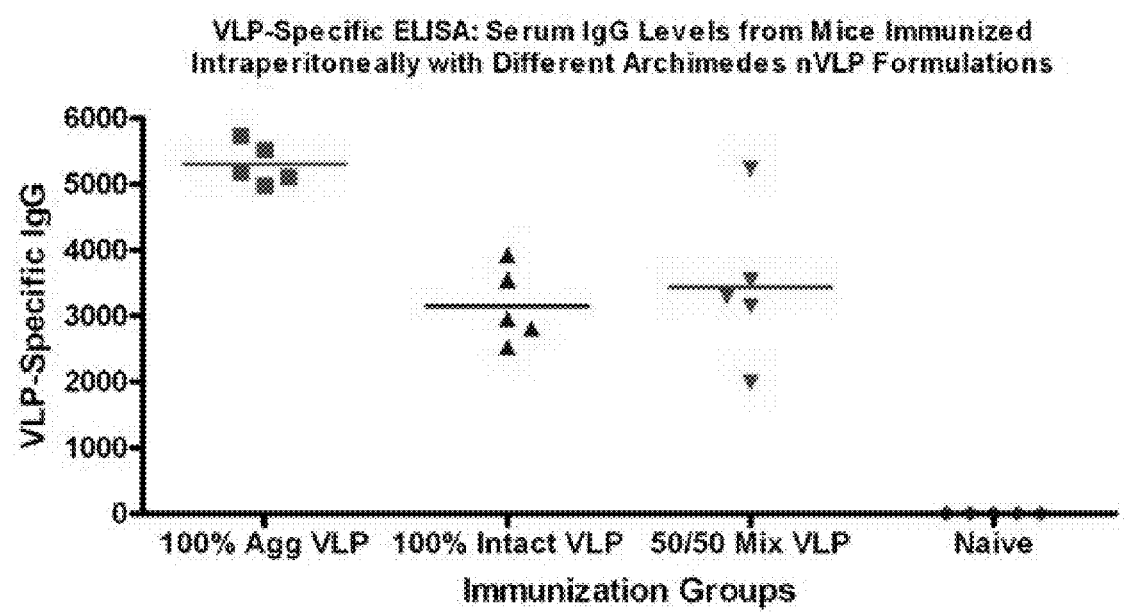
FIG. 5 illustrates VLP-specific IgG measured by ELISA.

The present invention relates to Norovirus antigenic and vaccine compositions and methods of preparing the compositions. In particular, the present invention provides a composition that comprises a Norovirus antigen and at least one adjuvant. Additionally or alternatively, the composition may further comprise at least one delivery agent. The invention also provides methods of administering the composition to an animal to produce an immune response or generate antibodies to Norovirus antigens.

Norovirus Antigens

The invention provides a composition comprising one or more Norovirus antigens. By "Norovirus," "Norovirus (NOR)," "norovirus," and grammatical equivalents herein, are meant members of the genus Norovirus of the family Caliciviridae. In some embodiments, a Norovirus can include a group of related, positive-sense single-stranded RNA, nonenveloped viruses that can be infectious to human or non-human mammalian species. In some embodiments, a Norovirus can cause acute gastroenteritis in humans. Noroviruses also can be referred to as small round structured viruses (SRSVs) having a defined surface structure or ragged edge when viewed by electron microscopy. Included within the Noroviruses are at least four genogroups (GI-IV) defined by nucleic acid and amino acid sequences, which comprise 15 genetic clusters. The major genogroups are GI and GII. GIII and GIV are proposed but generally accepted. Representative of GIII is the bovine, Jena strain. GIV contains one virus, Alphatron, at this time. For a further description of Noroviruses see Vinje et al. J. Clin. Micro. 41:1423-1433 (2003). By "Norovirus" also herein is meant recombinant Norovirus virus-like particles (rNOR VLPs). In some embodiments, the recombinant Norovirus VLPs are produced in an expression system using a Norovirus nucleic acid sequence, which encodes at least one capsid protein or fragment thereof. In other embodiments, recombinant expression of at least the Norovirus capsid protein encoded by ORF2 in cells, e.g., from a baculovirus vector in Sf9 cells, can result in spontaneous self-assembly of the capsid protein into VLPs. In yet other embodiments, recombinant expression of at least the Norovirus proteins encoded by ORF1 and ORF2 in cells, e.g., from a baculovirus vector in Sf9 cells, can result in spontaneous self-assembly of the capsid protein into VLPs. The Norovirus nucleic acid sequence may also be a consensus sequence comprising various Norovirus strains or a synthetic construct modified to enhance yields or stability, or improve antigenic or immunogenic properties of the encoded antigen. VLPs are structurally similar to Noroviruses but lack the viral RNA genome and therefore are not infectious. Accordingly, "Norovirus" includes virions that can be infectious or non-infectious particles, which include defective particles.

Non-limiting examples of Noroviruses include Norwalk virus (NV, GenBank M87661, $NP_{056821}$), Southampton virus (SHV, GenBank L07418), Desert Shield virus (DSV, U04469), Hesse virus (HSV), Chiba virus (CHV, GenBank AB042808), Hawaii virus (HV, GenBank U07611), Snow Mountain virus (SMV, GenBank U70059), Toronto virus (TV, Leite et al., Arch. Virol. 141:865-875), Bristol virus (BV), Jena virus (JV, AJ01099), Maryland virus (MV, AY032605), Seto virus (SV, GenBank AB031013), Camberwell (CV, AF145896), Lordsdale virus (LV, GenBank X86557), Grimsby virus (GrV, AJ004864), Mexico virus (MXV, GenBank U22498), Boxer (AF538679), C59 (AF435807), VA115 (AY038598), BUDS (AY660568), Houston virus (HoV), Minerva strain (EF126963.1), Laurens strain (EF126966.1), MOH (AF397156), Parris Island (PiV; AY652979), VA387 (AY038600), VA207 (AY038599), and Operation Iraqi Freedom (OIF, AY675554). The nucleic acid and corresponding amino acid sequences of each are all incorporated by reference in their entirety. In some embodiments, a cryptogram can be used for identification purposes and is organized: host species from which the virus was isolated/genus abbreviation/species abbreviation/strain name/year of occurrence/country of origin. (Green et al., Human Caliciviruses, in Fields Virology Vol. 1 841-874 (Knipe and Howley, editors-in-chief, 4th ed., Lippincott Williams & Wilkins 2001)). Use of a combination of Norovirus genogroups such as a genogroup I.1 (Norwalk virus) and 11.4 (Houston virus) or other commonly circulating strains, or synthetic constructs representing combinations or portions thereof are preferred in some embodiments. New strains of Noroviruses are routinely identified (Centers for Disease Control, Morbidity and Mortality Weekly Report, 56(33):842-846 (2007)) and consensus sequences of two or more viral strains may also be used to express Norovirus antigens.

The Norovirus antigen may be in the form of peptides, proteins, or virus-like particles (VLPs). In a preferred embodiment, the Norovirus antigen comprises VLPs. As used herein, "virus-like particle(s) or VLPs" refer to a virus-like particle(s), fragment(s), aggregates, or portion(s) thereof produced from the capsid protein coding sequence of Norovirus and comprising antigenic characteristic(s) similar to those of infectious Norovirus particles. Norovirus antigens may also be in the form of capsid monomers, capsid multimers, protein or peptide fragments of VLPs, or aggregates or mixtures thereof. The Norovirus antigenic proteins or peptides may also be in a denatured form, produced using methods known in the art.

Norovirus antigens may also include variants of the said capsid proteins or fragments thereof expressed on or in the VLPs of the invention. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

General texts which describe molecular biological techniques, which are applicable to the present invention, such as cloning, mutation, and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating of capsid proteins of Norovirus. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids including concensus sequences that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like.

The VLPs of the present invention can be formed from either the full length Norovirus capsid protein such as VP1 and/or VP2 proteins or certain VP1 or VP2 derivatives using standard methods in the art. Alternatively, the capsid protein used to form the VLP is a truncated capsid protein. In some embodiments, for example, at least one of the VLPs comprises a truncated VP1 protein. In other embodiments, all the VLPs comprise truncated VP1 proteins. The truncation may be an N- or C-terminal truncation. Truncated capsid proteins are suitably functional capsid protein derivatives. Functional capsid protein derivatives are capable of raising an immune response (if necessary, when suitably adjuvanted) in the same way as the immune response is raised by a VLP consisting of the full length capsid protein.

VLPs may contain major VP1 proteins and/or minor VP2 proteins. Preferably each VLP contains VP1 and/or VP2 protein from only one Norovirus genogroup giving rise to a monovalent VLP. As used herein, the term "monovalent" means the antigenic proteins are derived from a single Norovirus genogroup. For example, the VLPs contain VP1 and/or VP2 from a virus strain of genogroup I (e.g., VP1 and VP2 from Norwalk virus). Preferably the VLP is comprised of predominantly VP1 proteins. In one embodiment of the invention, the antigen is a mixture of monovalent VLPs wherein the composition includes VLPs comprised of VP1 and/or VP2 from a single Norovirus genogroup mixed with VLPs comprised of VP1 and/or VP2 from a different Norovirus genogroup taken from multiple viral strains (e.g. Norwalk virus and Houston virus). Purely by way of example the composition can contain monovalent VLPs from one or more strains of Norovirus genogroup I together with monovalent VLPs from one or more strains of Norovirus genogroup II. Preferably, the Norovirus VLP mixture is composed of the strains of Norwalk and Houston Noroviruses.

However, in an alternative embodiment of the invention, the VLPs may be multivalent VLPs that comprise, for example, VP1 and/or VP2 proteins from one Norovirus genogroup intermixed with VP1 and/or VP2 proteins from a second Norovirus genogroup, wherein the different VP1 and VP2 proteins are not chimeric VP1 and VP2 proteins, but associate together within the same capsid structure to form immunogenic VLPs. As used herein, the term "multivalent" means that the antigenic proteins are derived from two or more Norovirus genogroups. Multivalent VLPs may contain VLP antigens taken from two or more viral strains. Purely by way of example the composition can contain multivalent VLPs comprised of capsid monomers or multimers from one or more strains of Norovirus genogroup I together with capsid monomers or multimers from one or more strains of Norovirus genogroup II. Preferably, the multivalent VLPs contain capsid proteins from the strains of Norwalk and Houston Noroviruses.

The combination of monovalent or multivalent VLPs within the composition preferably would not block the immunogenicity of each VLP type. In particular it is preferred that there is no interference between Norovirus VLPs in the combination of the invention, such that the combined VLP composition of the invention is able to elicit immunity against infection by each Norovirus genotype represented in the vaccine. Suitably the immune response against a given VLP type in the combination is at least 50% of the immune response of that same VLP type when measured individually, preferably 100% or substantially 100%. The immune response may suitably be measured, for example, by antibody responses, as illustrated in the examples herein.

Multivalent VLPs may be produced by separate expression of the individual capsid proteins followed by combination to form VLPs. Alternatively multiple capsid proteins may be expressed within the same cell, from one or more DNA constructs. For example, multiple DNA constructs may be transformed or transfected into host cells, each vector encoding a different capsid protein. Alternatively a single vector having multiple capsid genes, controlled by a shared promoter or multiple individual promoters, may be used. IRES elements may also be incorporated into the vector, where appropriate. Using such expression strategies, the co-expressed capsid proteins may be co-purified for subsequent VLP formation, or may spontaneously form multivalent VLPs which can then be purified.

A preferred process for multivalent VLP production comprises preparation of VLP capsid proteins or derivatives, such as VP1 and/or VP2 proteins, from different Norovirus genotypes, mixing the proteins, and assembly of the proteins to produce multivalent VLPs. The capsid proteins may be in the form of a crude extract, be partially purified or purified prior to mixing. Assembled monovalent VLPs of different genogroups may be disassembled, mixed together and reassembled into multivalent VLPs. Preferably the proteins or VLPs are at least partially purified before being combined. Optionally, further purification of the multivalent VLPs may be carried out after assembly.

Suitably the VLPs of the invention are made by disassembly and reassembly of VLPs, to provide homogenous and pure VLPs. In one embodiment multivalent VLPs may be made by disassembly of two or more VLPs, followed by combination of the disassembled VLP components at any suitable point prior to reassembly. This approach is suitable when VLPs spontaneously form from expressed VP1 protein, as occurs for example, in some yeast strains. Where the expression of the VP1 protein does not lead to spontaneous VLP formation, preparations of VP1 proteins or capsomers may be combined before assembly into VLPs.

Where multivalent VLPs are used, preferably the components of the VLPs are mixed in the proportions in which they are desired in the final mixed VLP. For example, a mixture of the same amount of a partially purified VP1 protein from Norwalk and Houston viruses (or other Norovirus strains) provides a multivalent VLP with approximately equal amounts of each protein.

Compositions comprising multivalent VLPs may be stabilized by solutions known in the art, such as those of WO 98/44944, WO0045841, incorporated herein by reference.

Compositions of the invention may comprise other proteins or protein fragments in addition to VP1 and VP2 proteins or derivatives. Other proteins or peptides may also be co-administered with the composition of the invention. Optionally the composition may also be formulated or co-administered with non-Norovirus antigens. Suitably these antigens can provide protection against other diseases.

The VP1 protein or functional protein derivative is suitably able to form a VLP, and VLP formation can be assessed by standard techniques such as, for example, electron microscopy and dynamic laser light scattering.

Antigen Preparation

The antigenic molecules of the present invention can be prepared by isolation and purification from the organisms in which they occur naturally, or they may be prepared by recombinant techniques. Preferably the Norovirus VLP antigens are prepared from insect cells such as Sf9 or H5 cells, although any suitable cells such as *E. coli* or yeast cells, for example, *S. cerevisiae, S. pombe, Pichia pastori* or other *Pichia* expression systems, mammalian cell expression such as CHO or HEK systems may also be used. When prepared by a recombinant method or by synthesis, one or more insertions, deletions, inversions or substitutions of the amino acids constituting the peptide may be made. Each of the aforementioned antigens is preferably used in the substantially pure state.

The procedures of production of norovirus VLPs in insect cell culture have been previously disclosed in U.S. Pat. No. 6,942,865, which is incorporated herein by reference in its entirety. Briefly, a cDNA from the 3' end of the genome containing the viral capsid gene (ORF2) and a minor structural gene (ORF3) were cloned. The recombinant baculoviruses carrying the viral capsid genes were constructed from the cloned cDNAs. Norovirus VLPs were produced in Sf9 or H5 insect cell cultures.

Adjuvants

The invention further provides a composition comprising adjuvants for use with the Norovirus antigen. Most adjuvants contain a substance designed to protect the antigen from rapid catabolism, such as aluminum hydroxide or mineral oil, and a stimulator of immune responses, such as Bordatella pertussis or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; and Quil A.

Suitable adjuvants also include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, and liposomes. Preferably, the adjuvants are not bacterially-derived exotoxins. Preferred adjuvants are those which stimulate a Th1 type response such as 3DMPL or QS21.

Monophosphoryl Lipid A (MPL), a non-toxic derivative of lipid A from *Salmonella*, is a potent TLR-4 agonist that has been developed as a vaccine adjuvant (Evans et al. 2003). In preclinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MPL in intranasal formulations should provide rapid induction of innate responses, eliciting nonspecific immune responses from viral challenge while enhancing the specific responses generated by the antigenic components of the vaccine.

Accordingly, in one embodiment, the present invention provides a composition comprising monophosphoryl lipid A (MPL®) or 3 De-O-acylated monophosphoryl lipid A (3D-MPL®) as an enhancer of adaptive and innate immunity. Chemically 3D-MPL® is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a composition comprising synthetic lipid A, lipid A mimetics or analogs, such as BioMira's PET Lipid A, or synthetic derivatives designed to function like TLR-4 agonists.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation. Suitably effective increases in immunoglobulin levels include by more than 5%, preferably by more than 25%, and in particular by more than 50%, as compared to the same antigen composition without any adjuvant.

Deliver Agent

The invention also provides a composition comprising a delivery agent which functions to enhance antigen uptake based upon, but not restricted to, increased fluid viscosity due to the single or combined effect of partial dehydration of host mucopolysaccharides, the physical properties of the delivery agent, or through ionic interactions between the delivery agent and host tissues at the site of exposure, which provides a depot effect. Alternatively, the delivery agent can increase antigen retention time at the site of delivery (e.g., delay expulsion of the antigen). Such a delivery agent may be a bioadhesive agent. In particular, the bioadhesive may be a mucoadhesive agent selected from the group consisting of glycosaminoglycans (e.g., chondroitin sulfate, dermatan sulfate chondroitin, keratan sulfate, heparin, heparan sulfate, hyaluronan), carbohydrate polymers (e.g., pectin, alginate, glycogen, amylase, amylopectin, cellulose, chitin, stachyose, unulin, dextrin, dextran), cross-linked derivatives of poly(acrylic acid), polyvinyl alcohol, polyvinyl pyrollidone, polysaccharides (including mucin and other mucopolysaccharides) cellulose derivatives (e.g., hydroxypropyl methylcellulose, carboxymethylcellulose), proteins (e.g. lectins, fimbrial proteins), and deoxyribonucleic acid. Preferably, the mucoadhesive agent is a polysaccharide, such as chitosan, a chitosan salt, or chitosan base (e.g. chitosan glutamate).

Chitosan, a positively charged linear polysaccharide derived from chitin in the shells of crustaceans, is a bioadhesive for epithelial cells and their overlaying mucus layer. Formulation of antigens with chitosan increases their contact time with the nasal membrane, thus increasing uptake by virtue of a depot effect (Illum et al. 2001; 2003; Davis et al. 1999; Bacon et al. 2000; van der Lubben et al. 2001; 2001; Lim et al. 2001). Chitosan has been tested as a nasal delivery system for several vaccines, including influenza, pertussis and diphtheria, in both animal models and humans (Illum et al. 2001; 2003; Bacon et al. 2000; Jabbal-Gill et al. 1998; Mills et al. 2003; McNeela et al. 2004). In these trials, chitosan was shown to enhance systemic immune responses to levels equivalent to parenteral vaccination. In addition, significant antigen-specific IgA levels were also measured in mucosal secretions. Thus, chitosan can greatly enhance a nasal vaccine's effectiveness. Moreover, due to its physical characteristics, chitosan is particularly well suited to intranasal vaccines formulated as powders (van der Lubben et al. 2001; Mikszta et al. 2005; Huang et al. 2004).

Accordingly, in one embodiment, the present invention provides an antigenic or vaccine composition adapted for intranasal administration, wherein the composition includes antigen and optionally an effective amount of adjuvant. In preferred embodiments, the invention provides an antigenic or vaccine composition comprising Norovirus antigen such as Norovirus VLP, in combination with at least one delivery agent, such as chitosan, and at least one adjuvant, such as MPL®, CPGs, imiquimod, gardiquimod, or synthetic lipid A or lipid A mimetics or analogs.

The molecular weight of the chitosan may be between 10 kDa and 800 kDa, preferably between 100 kDa and 700 kDa and more preferably between 200 kDa and 600 kDa. The concentration of chitosan in the composition will typically be up to about 80% (w/w), for example, 5%, 10%, 30%, 50%, 70% or 80%. The chitosan is one which is preferably at least 75% deacetylated, for example 80-90%, more preferably 82-88% deacetylated, particular examples being 83%, 84%, 85%, 86% and 87% deacetylation.

Vaccine and Antigenic Formulations

The compositions of the invention can be formulated for administration as vaccines or antigenic formulations. As used herein, the term "vaccine" refers to a formulation which contains Norovirus VLPs or other Norovirus antigens of the present invention as described above, which is in a form that is capable of being administered to a vertebrate and which induces an immune response sufficient to induce a therapeutic immunity to ameliorate an infection and/or to reduce at least one symptom of an infection and/or to enhance the efficacy of another dose of VLPs or antigen. As used herein, the term "antigenic formulation" or "antigenic composition" refers to a preparation which, when administered to a vertebrate, e.g. a mammal, will induce an immune response. As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-lymphocytes and/or other cells, such as macrophages, against an infectious agent, exhibited by a vertebrate (e.g., a human), that prevents or ameliorates infection or reduces at least one symptom thereof. Vaccine preparation is generally described in Vaccine Design ("The subunit and adjuvant approach" (eds Powell M. F. & Newman M. J.) (1995) Plenum Press New York). The compositions of the present invention can be formulated, for example, for delivery to one or more of the oral, gastro-intestinal, and respiratory (e.g. nasal) mucosa.

Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

In one embodiment, the Norovirus vaccine or antigenic formulation of the present invention may be formulated as a dry powder containing one or more Norovirus genogroup antigen(s) as the immunogen, an adjuvant such as MPL®, a biopolymer such as chitosan to promote adhesion to mucosal surfaces, and bulking agents such as mannitol and sucrose. For example, the Norovirus vaccine may be formulated as 10 mg of a dry powder containing one or more Norovirus genogroup antigen(s) (e.g., Norwalk virus, Houston virus, Snow Mountain virus), MPL® adjuvant, chitosan mucoadhesive, and mannitol and sucrose as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 µg MPL® (0.1 to 5% w/w range), and about 100 µg Norovirus antigen (0.05 to 5% w/w range).

Norovirus antigen may be present in a concentration of from about 0.01% (w/w) to about 80% (w/w). In one embodiment, Norovirus antigens can be formulated at dosages of about 5 µg, about 15 µg, and about 50 µg per 10 mg dry powder formulation (0.025, 0.075 and 0.25% w/w) for administration into both nostrils or about 10 µg, about 30 µg, and about 100 µg (0.1, 0.3 and 1.0% w/w) for administration into one nostril. The formulation may be given in one or both nostrils during each administration. There may be a booster administration 1 to 12 weeks after the first administration to improve the immune response. The content of the Norovirus antigens in the vaccine and antigenic formulations may be in the range of 1 μg to 100 mg, preferably in the range 1-500 μg, more preferably 5-200 μg, most typically in the range 10-100 μg. Total Norovirus antigen administered at each dose will be either about 10 μg, about 30 μg, or about 100 μg in a total of 20 mg dry powder when administered to both nostrils or 10 mg dry powder when administered to one nostril. Dry powder characteristics are such that less than 10% of the particles are less than 10 μm in diameter. Mean particle sizes range from 10 to 500 μm in diameter.

In another embodiment, the antigenic and vaccine compositions can be formulated as a liquid for subsequent administration to a subject. A liquid formulation intended for intranasal administration would comprise Norovirus genogroup antigen(s), adjuvant, and a delivery agent such as chitosan. Liquid formulations for intramuscular (i.m.) or oral administration would comprise Norovirus genogroup antigen(s), adjuvant, and a buffer, without a delivery agent (e.g., chitosan).

Preferably the antigenic and vaccine compositions hereinbefore described are lyophilized and stored anhydrous until they are ready to be used, at which point they are reconstituted with diluent, if used in a liquid formulation. Alternatively, different components of the composition may be stored separately in a kit or device (any or all components being lyophilized). The components may remain in lyophilized form for dry formulation or be reconstituted for liquid formulations, and either mixed prior to use or administered separately to the patient. For dry powder administration the vaccine or antigenic formulation may be pre-loaded into an intranasal delivery device or topical (e.g., dermal) delivery patch and stored until used. Preferably, such delivery device and associated packaging would protect and ensure the stability of its contents.

The lyophilization of antigenic formulations and vaccines is well known in the art. Typically the liquid antigen is freeze dried in the presence of agents to protect the antigen during the lyophilization process and to yield powders with desirable characteristics. Sugars such as sucrose, mannitol, trehalose, or lactose (present at an initial concentration of 10-200 mg/mL) are commonly used for cryoprotection and lyoprotection of protein antigens and to yield lyophilized cake or powders with desirable characteristics. Lyophilized compositions are theoretically more stable. Other drying technologies, such as spray drying or spray freeze drying may also be used. While the goal of most formulation processes is to minimize protein aggregation and degradation, the inventors have demonstrated that the presence of aggregated antigen enhances the immune response to Norovirus VLPs (see Examples 3 and 4 in animal models). Therefore, the inventors have developed methods by which the percentage of aggregation of the antigen can be controlled during the lyophilization process to produce an optimal ratio of aggregated antigen to intact antigen to induce a maximal immune response in animal models.

Thus, the invention also encompasses a method of making Norovirus antigen formulations comprising (a) preparing a pre-lyophilization solution comprising Norovirus antigen, sucrose, and chitosan, wherein the ratios of sucrose to chitosan are from about 0:1 to about 10:1; (b) freezing the solution; and (c) lyophilizing the frozen solution for 30-72 hours, wherein the final lyophilized product contains a percentage of said Norovirus antigen in aggregated form. The lyophilization may occur at ambient temperature, reduced temperature, or proceed in cycles at various temperatures. For illustration purposes only, lyophilization may occur over a series of steps, for instance a cycle starting at −69° C., gradually adjusting to −24° C. over 3 hours, then retaining this temperature for 18 hours, then gradually adjusting to −16° C. over 1 hour, then retaining this temperature for 6 hours, then gradually adjusting to +34° C. over 3 hours, and finally retaining this temperature over 9 hours In one embodiment, the pre-lyophilization solution further comprises a bulking agent. In another embodiment, said bulking agent is mannitol.

Appropriate ratios of sucrose and chitosan to yield desired percentages of aggregation can be determined by the following guidelines. A pre-lyophilization mixture containing mass ratios of sucrose to chitosan in a range from about 2:1 to about 10:1 will yield a range of about 50% to 100% intact Norovirus antigen (i.e. 0% to 50% aggregated antigen) post-lyophilization depending on pre-lyophilization solution concentrations (see Example 13). Mass ratios of 0:1 sucrose to chitosan will produce less than 30% of intact Norovirus antigen (i.e. greater than 70% aggregated antigen). Omission of both sucrose and chitosan and use of only a bulking agent, such as mannitol, will produce less than 10% intact antigen (i.e. greater than 90% aggregated antigen depending on pre-lyophilization solution concentrations). Using these guidelines, the skilled artisan could adjust the sucrose to chitosan mass ratios and concentrations in the pre-lyophilization mixture to obtain the desired amount of aggregation necessary to produce an optimal immune response.

In addition, the inclusion of sucrose, chitosan, and mannitol in the pre-lyophilization solution has no negative effect on the stability of the intact Norovirus antigen over time, i.e. the ratio of aggregated antigen/intact antigen in the formulation does not increase when stored as a dry powder for a period of about 12 months or greater (see Example 10). Thus, this lyophilization procedure ensures stable formulations with predictable and controllable ratios of aggregated to intact Norovirus antigen.

Methods of Stimulating an Immune Response

The amount of antigen in each antigenic or vaccine formulation dose is selected as an amount which induces a robust immune response without significant, adverse side effects. Such amount will vary depending upon which specific antigen(s) is employed, route of administration, and adjuvants used. In general, the dose administered to a patient, in the context of the present invention should be sufficient to effect a beneficial therapeutic response in the patient over time, or to induce the production of antigen-specific antibodies. Thus, the composition is administered to a patient in an amount sufficient to elicit an immune response to the specific antigens and/or to alleviate, reduce, or cure symptoms and/or complications from the disease or infection. An amount adequate to accomplish this is defined as a "therapeutically effective dose."

For a substantially pure form of the Norovirus antigen, it is expected that each dose will comprise about 1 μg to 10 mg, preferably about 2-50 μg for each Norovirus antigen in the formulation. In a typical immunization regime employing the antigenic preparations of the present invention, the formulations may be administered in several doses (e.g. 1-4), each dose containing 1-100 μg of each antigen. The dose will be determined by the immunological activity the composition produced and the condition of the patient, as well as the body weight or surface areas of the patient to be treated. The size of the dose also will be determined by the existence, nature, and extent of any adverse side effects that may accompany the administration of a particular composition in a particular patient.

The antigenic and vaccine formulations of the present invention may be administered via a non-mucosal or mucosal route. These administrations may include in vivo administration via parenteral injection (e.g. intravenous, subcutaneous, and intramuscular) or other traditional direct routes, such as buccal/sublingual, rectal, oral, nasal, topical (such as transdermal and ophthalmic), vaginal, pulmonary, intraarterial, intraperitoneal, intraocular, or intranasal routes or directly into a specific tissue. Alternatively, the vaccines of the invention may be administered by any of a variety of routes such as oral, topical, subcutaneous, mucosal, intravenous, intramuscular, intranasal, sublingual, transcutaneous, subdermal, intradermal and via suppository. Administration may be accomplished simply by direct administration using a patch, needle, catheter or related device, at a single time point or at multiple time points.

In a preferred embodiment, the antigenic and vaccine formulations of the present invention are administered to a mucosal surface. Immunization via the mucosal surfaces offers numerous potential advantages over other routes of immunization. The most obvious benefits are 1) mucosal immunization does not require needles or highly-trained personnel for administration, and 2) immune responses are raised at the site(s) of pathogen entry, as well as systemically (Isaka et al. 1999; Kozlowski et al. 1997; Mestecky et al. 1997; Wu et al. 1997).

In a further aspect, the invention provides a method of eliciting an IgA mucosal immune response and an IgG systemic immune response by administering (preferably intranasally or orally) to a mucosal surface of the patient an antigenic or vaccine composition comprising one or more Norovirus antigens, at least one effective adjuvant and/or at least one delivery agent.

The present invention also contemplates the provision of means for dispensing intranasal formulations of Norovirus antigens hereinbefore defined, and at least one adjuvant or at least one delivery agent as hereinbefore defined. A dispensing device may, for example, take the form of an aerosol delivery system, and may be arranged to dispense only a single dose, or a multiplicity of doses. Such a device would deliver a metered dose of the vaccine or antigenic formulation to the nasal passage. Other examples of appropriate devices include, but are not limited to, droppers, swabs, aerosolizers, insufflators (e.g. Valois Monopowder Nasal Administration Device, Bespak UniDose DP), nebulizers, and inhalers. The devices may deliver the antigenic or vaccine formulation by passive means requiring the subject to inhale the formulation into the nasal cavity. Alternatively, the device may actively deliver the formulation by pumping or spraying a dose into the nasal cavity. The antigenic formulation or vaccine may be delivered into one or both nostrils by one or more such devices. Administration could include two devices per subject (one device per nostril). Actual dose of active ingredient (Norovirus antigen) may be about 5-1000 µg. In a preferred embodiment, the antigenic or vaccine formulation is administered to the nasal mucosa by rapid deposition within the nasal passage from a device containing the formulation held close to or inserted into the nasal passageway.

The invention also provides a method of generating antibodies to one or more Norovirus antigens, said method comprising administration of a vaccine or antigenic formulation of the invention as described above to a subject. These antibodies can be isolated and purified by routine methods in the art. The isolated antibodies specific for Norovirus antigens can be used in the development of diagnostic immunological assays. These assays could be employed to detect a Norovirus in clinical samples and identify the particular virus causing the infection (e.g. Norwalk, Houston, Snow Mountain, etc.). Alternatively, the isolated antibodies can be administered to subjects susceptible to Norovirus infection to confer passive or short-term immunity.

As mentioned above, the vaccine formulations of the invention may be administered to a subject to treat symptoms of a Norovirus infection. Symptoms of Norovirus infection are well known in the art and include nausea, vomiting, diarrhea, and stomach cramping. Additionally, a patient with a Norovirus infection may have a low-grade fever, headache, chills, muscle aches, and fatigue. The invention encompasses a method of inducing an immune response in a subject experiencing a Norovirus infection by administering to the subject a vaccine formulation of the invention such that at least one symptom associated with the Norovirus infection is alleviated and/or reduced. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a Norovirus infection or additional symptoms, a reduced severity of Norovirus symptoms or suitable assays (e.g. antibody titer and/or T-cell activation assay). The objective assessment comprises both animal and human assessments.

EXAMPLES

The invention will now be illustrated in greater detail by reference to the specific embodiments described in the following examples. The examples are intended to be purely illustrative of the invention and are not intended to limit its scope in any way.

Example 1. Investigations into Immune Responses to Different Norovirus Antigen Forms To investigate the efficacy of the vaccine formulations, mice were immunized intranasally (i.n.) with liquid suspension vaccine formulation by micropipette. Mice received only a single vaccine dose (prime).

For the experiment, three vaccine formulations were prepared. The first, referred to as 100% aggregate, was prepared by lyophilization of VLPs under conditions that disrupt the native structure of the VLP and induce aggregation. The second, 100% intact, was prepared with rehydrated lyophilized placebo, spiked with 100% native monodisperse VLPs from non-lyophilized VLP stock. The third formulation, 50/50 Mix, is made either by mixing the previous two formulations at a ratio of 1:1, or by lyophilizing under conditions that yield ~50% intact and 50% aggregated VLPs. The structural state and concentration of the intact native VLP was assayed by size exclusion high performance liquid chromatography (SE-HPLC) and ultraviolet (UV) absorbance. The total protein concentration (which includes the aggregate) of the formulations was determined by quantitative staining of sodium dodecyl sulfate polyacrylamide gel electrophoresis (SDS-PAGE)-resolved proteins. Percent aggregated/intact was calculated as the ratio of intact native VLP to total protein.

TABLE 1

Mixtures shown below were prepared for Experiment
605.125, mouse i.n. liquid vaccination.

| Group number | Chitosan (mg/mL) | Mannitol (mg/mL) | Sucrose (mg/mL) | MPL (mg/mL) | Norwalk VLP (mg/mL) |
|---|---|---|---|---|---|
| 1 | 3.5 | 0.750 | 0.750 | 1.0 | 1.0 |
| 2 | 3.5 | 0.750 | 0.750 | 1.0 | 1.0 |
| 3 | 3.5 | 0.750 | 0.750 | 1.0 | 1.0 |
| 4 | 3.5 | 0.750 | 0.750 | 1.0 | 0 |

Table 1. Prime for exp 605.125 (mouse i.n.) Values indicate final concentrations of the formulations.
Dose: 20 μL per mouse, 10 μL per nare.
Group 1, 100% Agg: rehydrated 100% aggregated VLP
Group 2, 100% Intact: rehydrated lyophilized placebo, spiked with 100% intact VLPs from non-lyophilized VLP stock.
Group 3, 50/50 mix: 1:1 mixture of solutions from Groups 1 and 2.
Group 4, Naïve: rehydrated lyophilized placebo This experiment measures the immune response in mice to different Norovirus VLP formulations. Groups of mice (5 per group) were vaccinated intranasally (i.n.) once with rehydrated dry powder formulations shown in Table 1. Animals vaccinated with VLP-containing formulations received the same amount of total protein. 100% Agg (100% aggregated VLP protein); 100% Intact (100% native, monodisperse VLPs); 50/50 Mix (1:1 mixture of monodisperse and aggregated VLP); Naïve (no VLP protein). On day 14 following i.n. immunization, mice were euthanized, the cervical lymph nodes and spleens were harvested, and a single cell suspension was prepared for in vitro antigen-specific cell proliferation assays. In these assays the response of cervical lymph node cells or splenocytes were assessed to determine immunogenic responses against the antigen following in vivo immunization. Cervical lymph node cells or splenocytes were restimulated with either native monodisperse VLPs (native VLP, black bars) or heat-denatured VLP protein (ΔVLP, white bars) and the extent of cellular proliferation from each antigen form (100% Agg, 100% Intact, 50/50 Mix, or naïve) was measured by tritiated thymidine incorporation as indicated on the ordinate axis (CPM) (FIG. 1, cervical lymph node cells; FIG. 2, splenocytes).

Example 2. In Vitro Antigen-Specific Proliferation Assay

To further investigate the potency of the vaccine formulations, mice were immunized intraperitoneally (i.p.) with liquid suspension vaccine formulation. Mice received only a single vaccine dose (prime).

Similar to Example 1, groups of mice (5 per group) were vaccinated, but this time intraperitoneally (i.p.), once with rehydrated dry powder formulations shown in Table 2. Again, animals vaccinated with VLP-containing formulations received the same amount of total protein. 100% Agg (100% aggregated VLP protein); 100% Intact (100% native, intact VLPs); 50/50 Mix (1:1 mixture of intact and aggregated VLP); Naïve (no VLP protein).

TABLE 2

| Mixtures shown below were prepared for 605.127, mouse i.p. liquid immunization. | | | | | |
|---|---|---|---|---|---|
| Group number | Chitosan (mg/mL) | Mannitol (mg/mL) | Sucrose (mg/mL) | MPL (mg/mL) | Norwalk VLP (mg/mL) |
| 1 | 7 | 1.475 | 1.475 | 0.025 | 0.025 |
| 2 | 7 | 1.475 | 1.475 | 0.025 | 0.025 |
| 3 | 7 | 1.475 | 1.475 | 0.025 | 0.025 |
| 4 | 7 | 1.475 | 1.475 | 0.025 | 0 |

Prime for exp 605.127 (mouse i.p.) Values indicate final concentrations of the formulations and are equivalent to a single 10 mg delivery device.
Dose: 1 mL per mouse i.p.
Group 1, 100% Agg: rehydrated 100% aggregated VLP
Group 2, 100% Intact: rehydrated lyophilized placebo, spiked with 100% intact VLPs from non-lyophilized VLP stock.
Group 3, 50/50 mix: rehydrated from lyophilized 50/50 intact VLP/Aggregate
Group 4, Naïve: rehydrated lyophilized placebo In this assay, response of different murine cells to VLPs following in vivo immunization was measured. On day 14 following immunization, mice were euthanized, the spleens were harvested, and a single cell suspension was prepared. Splenocytes were restimulated with either intact, native VLPs (native VLP, dotted bars) or heat-denatured VLP protein (ΔVLP, white bars) and the extent of cellular proliferation from each antigen form (100% Agg, 100% Intact, 50/50 Mix, or naïve) was measured by tritiated thymidine incorporation as indicated on the ordinate axis (CPM) (FIG. 3). These data indicate that different biophysical forms of the VLPs prepared in the vaccine formulations elicit comparable T cell responses.

Example 3. VLP-Specific ELISPOT Assay

VLP-specific antibody-secreting cell (ASC) responses were measured from mice immunized intraperitoneally with different NV-VLP formulations described in Example 2. Groups of mice (5 per group) were vaccinated i.p. once with rehydrated dry powder formulations shown in Table 2 (Example 2). Animals vaccinated with VLP-containing formulations received the same amount of total protein. 100% Agg (100% aggregated VLP protein); 100% Intact (100% native, intact VLPs); 50/50 Mix (1:1 mixture of intact and aggregated VLP); Naïve (no VLP protein). On day 14, the mice were euthanized and the cervical lymph nodes were harvested. The cervical lymph node cells were cultured overnight on native, intact VLP-coated ELISPOT plates and were developed for either IgG or IgA-specific ELISPOTS using the appropriate HRP-conjugated secondary antibodies (FIG. 4). These data show that the three VLP antigen formulations all elicit an antigen-specific B cell response. The group immunized with 100% Agg VLPs exhibited the greatest immune response.

Example 4. VLP-Specific ELISA

Serum IgG levels were measured from mice immunized i.p. with different NV-VLP formulations. Groups of mice (5 per group) were vaccinated i.p. once with rehydrated dry powder formulations shown in Table 2 (Example 2). Animals vaccinated with VLP-containing formulations received the same amount of total protein. 100% Agg (100% aggregated VLP protein); 100% Intact (100% native, intact VLPs); 50/50 Mix (1:1 mixture of intact and aggregated VLP); Naïve (no VLP protein). On day 14, serum was collected and assayed by ELISA for anti-VLP-specific serum IgG (FIG. 5). These data correlate with the results shown in Example 3, indicating that the three VLP antigen formulations all elicit an antigen-specific B cell response. Again, the group immunized with 100% Agg VLPs showed the greatest immune response.

Example 5. Vaccine Formulations in Rabbits

Formulations were administered intranasally (i.n.) in rabbits using the Valois Monopowder Nasal Administration Device. The dry powder formulations are shown in Tables 3 and 4.

TABLE 3

Formulations described below were prepared for 605.129, rabbit i.n. dry powder (DP) vaccination.
Prime formulations for exp 605.129 (Rabbit i.n.) (final amounts for DP vaccines).

| Group number | Chitosan (mg/ 10 mg DP) | Mannitol (mg/ 10 mg) | Sucrose (mg/ 10 mg) | MPL (mg/ 10 mg) | Norwalk VLP (mg/ 10 mg) |
|---|---|---|---|---|---|
| 1 | 7 | 1.475 | 1.475 | 0.025 | 0.025 |
| 2 | 7 | 1.475 | 1.475 | 0.025 | 0.025 |
| 3 | 7 | 1.475 | 1.475 | 0.025 | 0.025 |
| 4 | 7 | 1.475 | 1.475 | 0.025 | 0 |

Values indicate final concentrations of the formulations based on a single device (10 mg DP) which is ½ total dose.
Dose: 20 mg DP per animal, 10 mg per nare.
Group 1, 100% Agg: 100% aggregated lyophilized VLP
Group 2, 100% Intact: 100% intact lyophilized VLP
Group 3, 50/50 mix: 50/50 intact/aggregate lyophilized VLP (not a mixture of 1 & 2)
Group 4, Naïve: placebo

TABLE 4

Formulations shown below were prepared for 605.129, rabbit i.n. dry powder (DP) vaccination.
Boost formulations for exp 605.129 (Rabbit i.n.) (final amounts for DP vaccines).

| Group number | Chitosan (mg/ 10 mg DP) | Mannitol (mg/ 10 mg) | Sucrose (mg/ 10 mg) | MPL (mg/ 10 mg) | Norwalk VLP (mg/ 10 mg) |
|---|---|---|---|---|---|
| 1 | 7 | 1.475 | 1.475 | 0.025 | 0.025 |
| 2 | 7 | 0 | 2.95 | 0.025 | 0.025 |
| 3 | 7 | 1.475 | 1.475 | 0.025 | 0.025 |
| 4 | 7 | 1.475 | 1.475 | 0.025 | 0 |

Values indicate final concentrations of the formulations based on a single device (10 mg DP) which is ½ total dose.
Dose: 20 mg DP per animal, 10 mg per nare.
Group 1, 100% Agg: 100% lyophilized aggregated VLP
Group 2, 100% Intact: 100% intact** VLP*
Group 3, 50/50 mix: 50/50 intact/aggregate lyophilized VLP (not a mixture of 1 & 2)
Group 4, Naïve: lyophilized placebo
*Formulated without mannitol to increase amount of intact VLP post lyophilization.
**Preparation yielded only ~80% intact VLP.

Example 6. Potency Assay of Norovirus Vaccine Formulation in Mice

Figure 6:
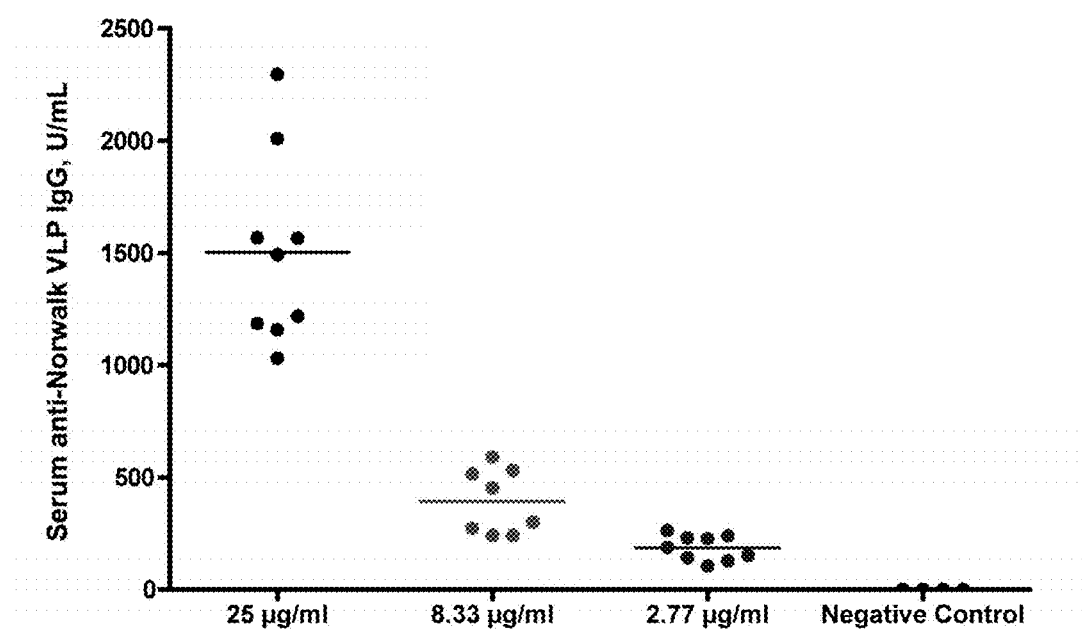
FIG. 6 illustrates the result of a potency assay for serum IgG response against Norwalk VLPs.

Female C57B16 mice were immunized intraperitoneally (i.p.) on day 0 with different dilutions of a reconstituted Norwalk VLP dry powder vaccine (containing Norwalk VLP, MPL and chitosan). Each animal was injected with 100 µL of the formulations indicated Serum was collected weekly and serum anti-VLP IgG measured by ELISA. Values for serum collected 3 weeks following immunization are shown in FIG. 6.

The value for each individual mouse is represented, with bars indicating the group mean. Serum anti-VLP IgG values correlated with the dose of vaccine indicated. This experimental design has been refined and developed as a potency assay required for the release of GMP manufactured vaccines for human clinical trials (FIG. 6).

Example 7. Potency of Liquid Vs. Reconstituted Norovirus Formulations in Mice Female C57B16 mice were immunized i.p. on day 0 with formulations that contained chitosan, mannitol, MPL, and various concentrations of Norwalk VLP (Table 5) in a volume of 100 µL. An internal standard curve was generated (groups 1-5) by solubilizing 10 mg/mL of dry powder matrix (mannitol, MPL, and chitosan) in purified water and adding the specified amounts of liquid Norwalk VLP. In contrast, the GMP VLP lots were previously lyophilized and then solubilized in 1.0 ml of purified water (groups 6-8). Serum was collected from mice on days 14, 21 and 30, and serum anti-Norwalk VLP IgG was measured by ELISA.

TABLE 5

Liquid and Reconstituted Norwalk Formulations used to immunize mice (i.p.).

| | | | Calculated Potency | | |
|---|---|---|---|---|---|
| Group | Treatment | 95% CI | Potency | Min | Max |
| 1 | 5 µg VLP in Placebo | 0.173 | 58.0 | 39.0 | 86.3 |
| 2 | 2.5 µg VLP in Placebo | 0.192 | 23.3 | 15.0 | 36.3 |
| 3 | 1.25 µg VLP in Placebo | 0.182 | 11.2 | 7.4 | 17.0 |
| 4 | 0.63 µg VLP in Placebo | 0.287 | 5.4 | 2.8 | 10.4 |
| 5 | 0.31 µg VLP in Placebo | 0.114 | 3.8 | 2.9 | 4.9 |
| 6 | 2.5 µg GMP lot | 0.276 | 11.3 | 6.0 | 21.3 |
| 7 | 7.5 µg GMP lot | 0.221 | 96.8 | 58.2 | 161.0 |
| 8 | 25 µg GMP lot | 0.147 | 113.6 | 80.9 | 159.5 |

Figure 7:
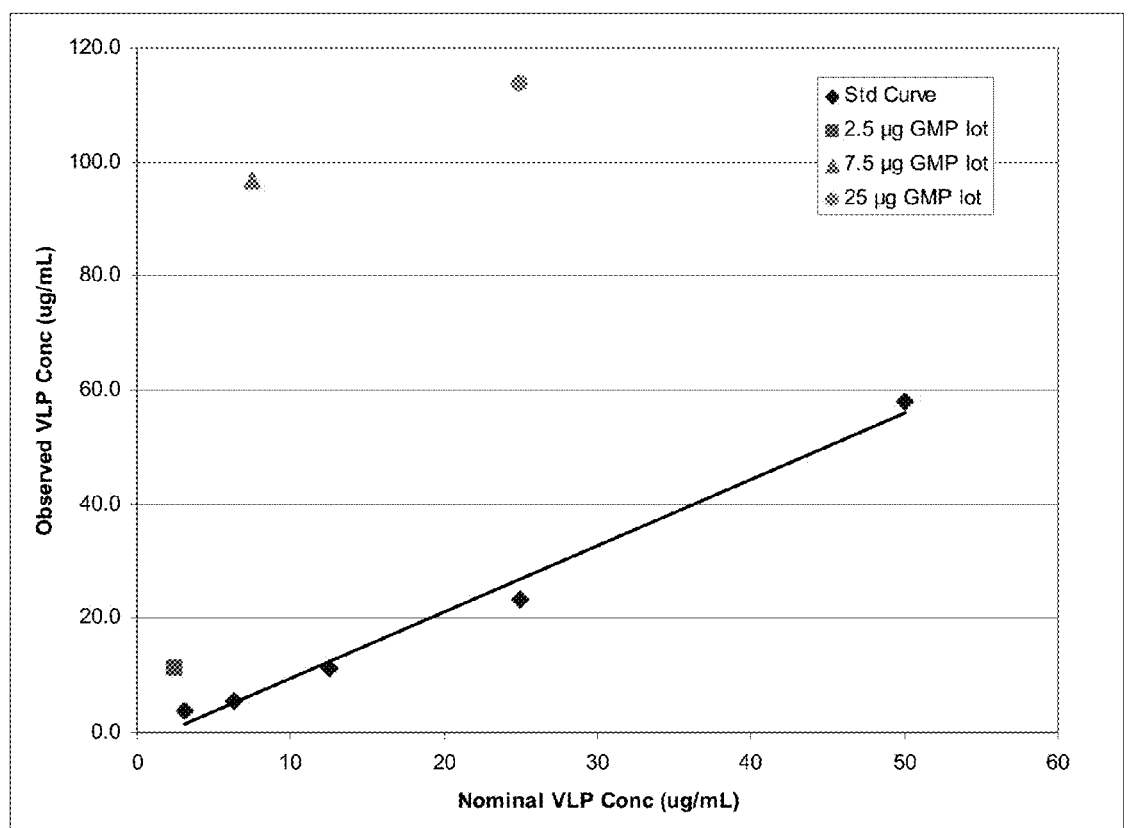
FIG. 7 depicts the results of a potency assay comparing serum IgG responses against Norwalk VLPs in mice immunized with either a liquid formulation of the antigen or a formulation reconstituted from dry powder. The graph shows potency versus concentration of Norwalk VLPs in the different formulations.

The relative potency for each formulation was calculated using the following formula: Inv Log (Ave.—Y intercept/slope). Potency is plotted against VLP concentration in the formulations and reported in relation to the standard curve generated using known amounts of VLP spiked into the matrix background (FIG. 7). The results shown are representative of 3 separate serum collection time points. These data indicate that the Norwalk VLP formulation reconstituted from dry powder has an overall higher potency than the liquid formulations.

Example 8. Potency of Dry Powder Formulation in Rabbits

Forty-three female New Zealand White rabbits were intranasally (i.n.) immunized using the Valois Monopowder Nasal Administration Device with either 5 µg (Low) or 25 µg (Hi) of Norwalk VLPs±MPL and ±chitosan formulated into dry powders. One group received the Hi dose of VLPs and MPL formulated as a liquid and administered intramuscularly (i.m.). Rabbits were vaccinated on days 0 and 21. MPL, when used, was used at the same dose as the VLPs (i.e., 5 µg Norwalk VLPs and 5 µg MPL). Chitosan, when used, was 7 mg/dose.

Figure 8:
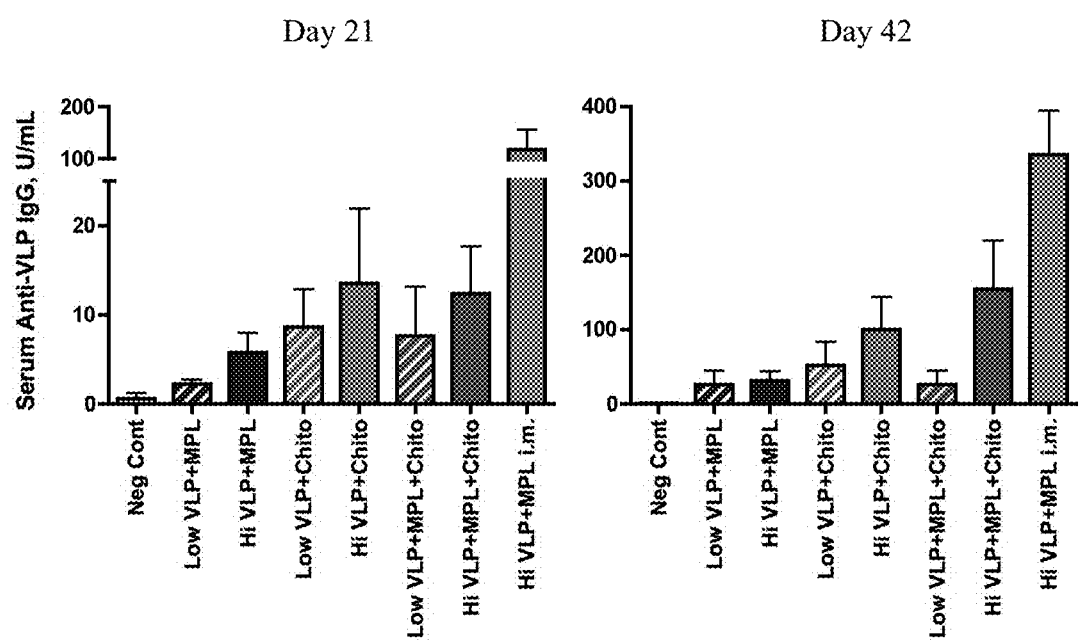
FIG. 8 shows the serum IgG response in rabbits on day 21 (left panel) and day 42 (right panel) following administration of different formulations of Norovirus VLP vaccine.
Figure 9:
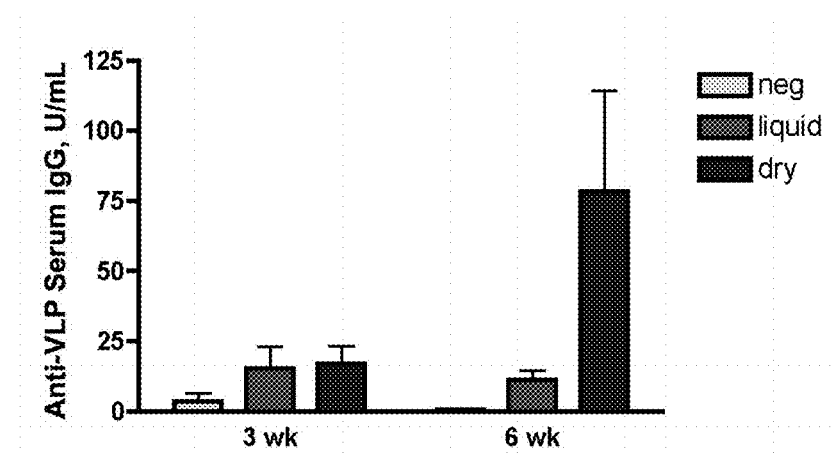
FIG. 9 illustrates the serum IgG response in rabbits immunized intranasally with either a liquid formulation or a dry powder formulation of Norwalk VLPs.
Figure 10:
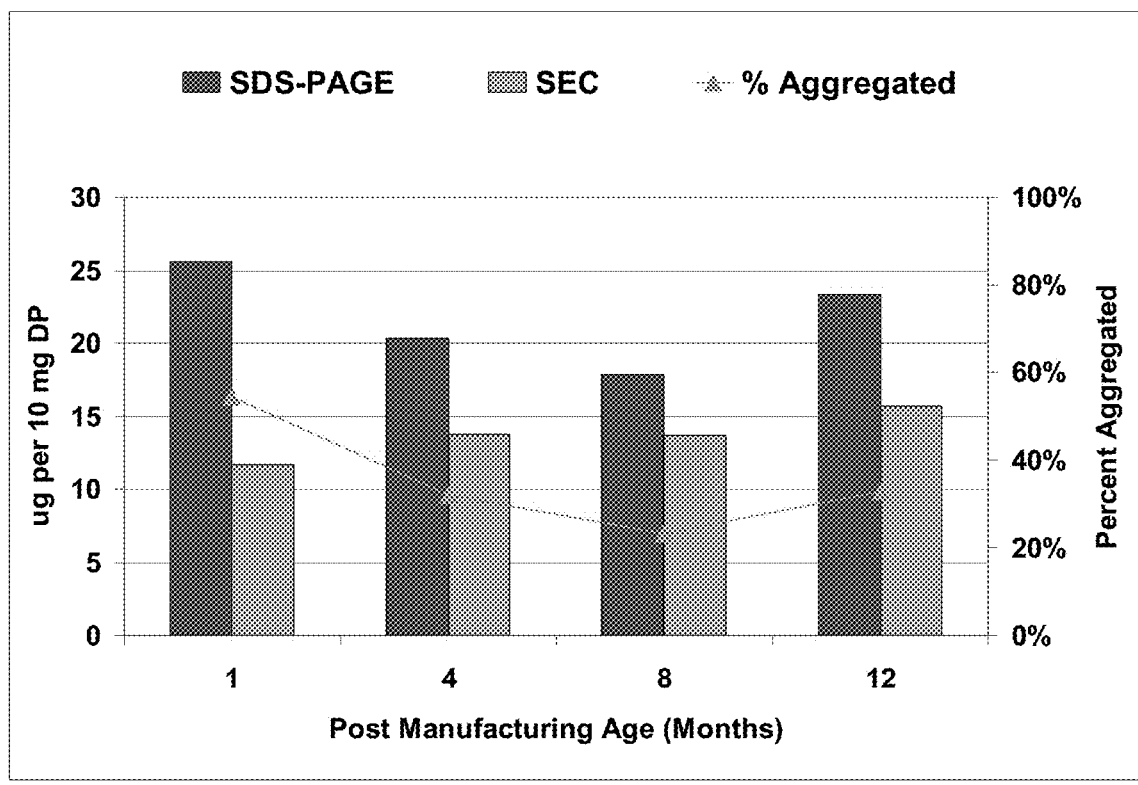
FIG. 10 depicts the stability of dry powder formulation as measured by quantitative SDS-PAGE analysis and size exclusion chromatography (SEC). Regression analysis indicates no statistical trends in either the total or intact μg VLP per 10 mg dry powder over 1 year. The percent aggregate is a calculation assuming that VLP protein not detected by SEC, compared to the total VLP protein by quantitative SDS-PAGE, is aggregated.
Figure 11:
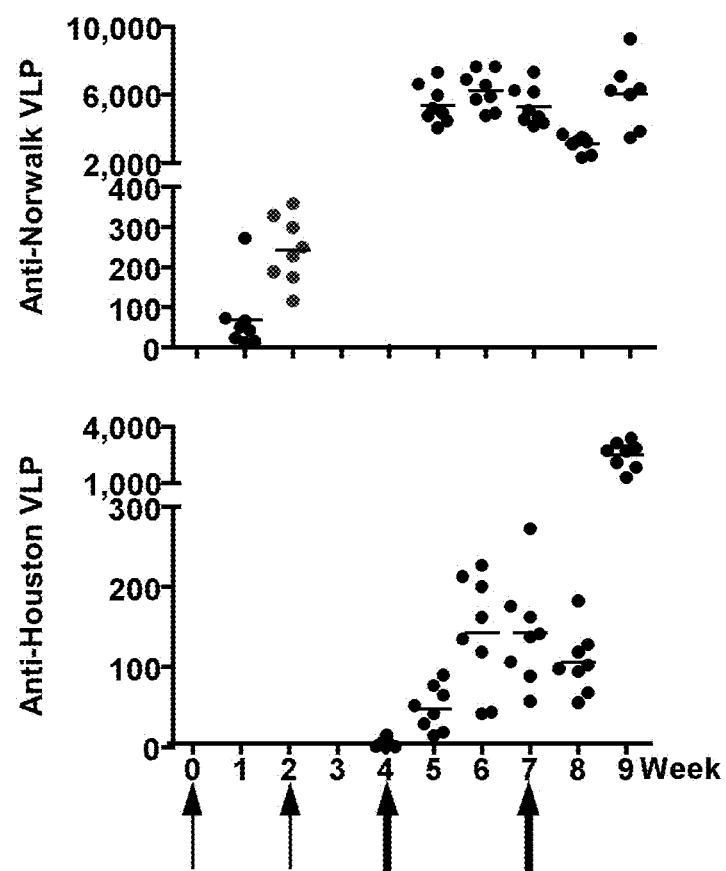
FIG. 11 illustrates the results of an ELISA assay of anti-Norovirus antibody response in mice immunized i.p. with multiple Norovirus antigens. The thin arrows indicate booster injections with formulations containing only Norwalk VLPs. The thick arrows denote booster injections with formulations containing both Norwalk and Houston VLPs.
Figure 12:
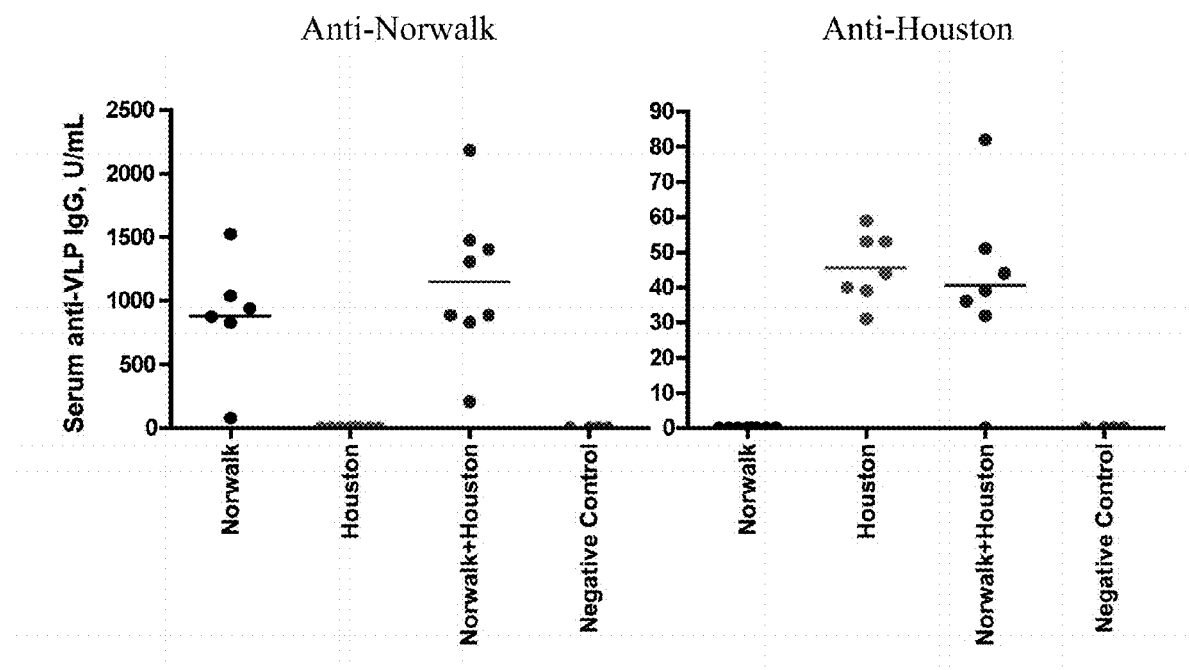
FIG. 12 illustrates an ELISA assay of anti-Norovirus antibody response in mice immunized i.p. with either Norwalk VLPs, Houston VLPs, or a combination of Norwalk and Houston VLPs.

Serum IgG specific for the Norwalk VLPs (as determined by ELISA) is shown in FIG. 8. Mean values for each treatment groups are shown for day 21 (left panel, collected just prior to administration of the booster immunization) and day 42 (right panel). Values are reported in U/mL of VLP-specific IgG, with 1 U approximating 1 µg. Standard deviations are indicated by bars. All treatment groups had 6 animals, except the negative control group (3 rabbits) and the intramuscularly immunized group (4 animals). These data show that generally the higher VLP dose results in greater serum anti-VLP IgG levels. Chitosan, in particular, enhances responses to intranasal vaccines. The i.m. immunized group showed the greatest responses. However, VLP-specific IgG levels in the intranasally immunized groups were also quite robust.

Example 9. Potency of Liquid Vs. Dry Norovirus Formulations Given Intranasally in Rabbits Female New Zealand White rabbits were intranasally immunized using the Valois Monopowder Nasal Administration Device with 50 μg of Norwalk VLPs+50 μg MPL+14 mg chitosan formulated into either a dry powder or a liquid. The vaccine content was identical, except for the physical state. Immunizations were on days 0 and 21 (weeks 0 and 3), with serum collected prior to the boost at 3 weeks, and again at 6 weeks following the initial vaccination. Serum IgG specific for Norwalk VLPs was measured by ELISA, and the results are shown in FIG. 9.

Group means are indicated, with the bars representing standard deviations. The dry powder immunization group had 6 rabbits, and the liquid immunization group had 10 rabbits. Eight negative control rabbits are represented. Little difference was seen between the liquid and dry powder immunization groups at 3 weeks; however, at 6 weeks following the initial immunization, rabbits immunized with the dry powder formulation had superior serum anti-VLP IgG responses compared to the liquid immunization group.

Example 10. Stability of Norovirus Dry Powder Formulations

To investigate the stability of the dry powder VLP formulation, bulk drug product was prepared by mixing (per 10 mg drug product) 25 μg of a Genogroup I VLP in solution with 25 μg MPL, 700 μg chitosan glutamate, 1.475 mg mannitol, and 1.475 mg sucrose. The solution was lyophilized, blended with an additional 6.3 mg chitosan glutamate (per 10 mg drug product), filled into Bespak unidose devices at a nominal 10 mg of dry powder, and stored in sealed foil pouches with desiccant capsules. Total VLP content was measured using Imperial stained SDS-PAGE and scanning densitometry, while size exclusion chromatography (SEC) was used to quantify intact VLP content. These measurements indicated that, within experimental error, no change in either total or intact VLP was detectable over the 12 month period (FIG. 10). Assuming that the lower VLP protein recovery by SEC, when compared to SDS-PAGE results, was due to aggregation, the calculated % aggregate did not increase with time but rather remained constant or decreased throughout the 12 months of storage. One of the more common stability issues with proteins is increased aggregation with storage. Based on the results in FIG. 10, it can be concluded that the formulation results in a stable percentage of intact VLPs allowing the product to be manufactured and used over at least a one year period.

Example 11. Multiple Norovirus Antigens

Eight C57Bl/6 mice (female, 9 weeks of age) were immunized intraperitoneally (IP) on days 0 and 14 with 2.5 μg Norwalk VLP formulated with 0.7 mg chitosan, 2.5 μg MPL and 0.3 mg mannitol brought to 0.1 mL with water. Two control mice were immunized with saline. On days 28 and 49, they were immunized again IP with 2.5 μg Norwalk VLP+2.5 μg Houston VLP formulated with 0.7 mg chitosan, 2.5 μg MPL and 0.3 mg mannitol brought to 0.1 mL with water. The control mice again received saline. Serum samples were collected weekly beginning on week 5 (day 35) and analyzed by ELISA for reactivity with Norwalk VLPs or Houston VLPs. The time of boost with the Norwalk only mixtures are indicated by the thin arrows, and the Norwalk+Houston VLP mixtures are indicated by thick arrows. Individual serum IgG responses specific for Norwalk VLPs (top panel) or Houston VLPs (bottom panel) in U/mL (with 1 U approximating 1 μg of IgG) are shown. Means are indicated by bars. Note that the Y-axis scales are different, as the anti-Norwalk responses were much more robust due to two previous immunizations on days 0 and 14 (weeks 0 and 2). However, the responses against Houston VLPs are quite robust, with a large increase appearing in the second week after the boost. These data demonstrate that specific immune responses can be generated against different antigenic strains of Norovirus VLPs in the same immunizing mixture. (FIG. 11).

Example 12. Immune Response to Different Norovirus Antigens

Female C57B16 mice were immunized intraperitoneally (IP) on days 0 and 14 with 25 μg Norwalk VLP, 25 μg Houston VLP, or a combination of 25 μg of each Norwalk and Houston VLP. Serum was collected weekly and serum anti-VLP IgG measured by ELISA. Values for serum collected 4 weeks following immunization are shown in FIG. 12.

VLP content of the immunizations is indicated on the X axis. The value for each individual mouse is represented, with bars indicating the group mean. Antibody levels are represented in U/mL, with 1 U approximating 1 μg of serum IgG. Values in the left panel were determined using Norwalk VLPs as the capture agent, while Houston VLPs were used to coat ELISA plates in order to measure the values on the right panel. These data show that immunization with Norwalk VLP does not lead to serum antibodies that are able to recognize Houston VLPs, or vice versa.

Example 13. Mixtures of Sucrose and Chitosan Preserve Norovirus VLP Structure in Dry Powder Formulations The following experiments examined the effects of sucrose, chitosan, and mannitol, alone or in combination, in pre-lyophilization solutions on the native Norwalk VLP quaternary structure during lyophilization. Table 6 is a composite of several experiments showing pre-lyophilization solution concentrations of the constituents of interest, the total volume of the mixture, and the corresponding mass ratios. All solutions were manually swirled and gently vortexed to homogeneity, then shell frozen in liquid nitrogen and lyophilized external to the unit using side-arm vessels for times ranging from about 30 to 60 hours.

TABLE 6

Pre-lyophilization solution mixtures used for testing the effects of different concentrations and combinations of sucrose, chitosan glutamate (chitosan) and mannitol on the structure of the quaternary structure the Norwalk VLP.

| Experiment and Sample | Solution concentrations of constituents pre-lyophilization (mg/mL) | | | | Total Volume (mL) | Mass equivalents S = sucrose C = chitosan M = mannitol | | |
|---|---|---|---|---|---|---|---|---|
| | Sucrose | Chitosan | Mannitol | VLP (protein) | | S | C | M |
| LE1 | 0 | 0 | 100 | 0.83 | 0.30 | 0 | 0 | 1 |
| LE2 | 0 | 0 | 75.0 | 0.62 | 0.40 | | | |
| LE3 | 0 | 0 | 50.0 | 0.42 | 0.60 | | | |
| LE4 | 0 | 0 | 25.0 | 0.21 | 1.20 | | | |
| LE5 | 0 | 0 | 10.0 | 0.08 | 3.00 | | | |
| LG1-LG3 | 0 | 7.83 | 0 | 0.20 | 1.28 | 0 | 1 | 0 |
| LG4-LG6 | 0 | 5.06 | 0 | 0.13 | 1.98 | | | |
| LG7-LG9 | 0 | 2.09 | 0 | 0.05 | 4.78 | | | |
| LG10 | 19.32 | 1.93 | 0 | 0.05 | 5.18 | 10 | 1 | 0 |
| LG11 | 10.05 | 2.01 | 0 | 0.05 | 4.98 | 5 | 1 | |
| LG12 | 5.13 | 2.05 | 0 | 0.05 | 4.88 | 2.5 | 1 | |
| LG13 | 9.52 | 0.00 | 0 | 0.09 | 2.63 | 1 | 0 | |
| LJ1-LJ2 | 5.29 | 2.51 | 0 | 0.09 | 2.79 | 2 | 1 | 0 |
| LJ3-LJ4 | 4.17 | 1.98 | 0 | 0.07 | 3.54 | | | |
| LJ5-LJ6 | 3.65 | 1.73 | 0 | 0.06 | 4.04 | | | |
| LJ7-LJ8 | 2.93 | 1.39 | 0 | 0.05 | 5.04 | | | |
| LJ9-LJ10 | 5.25 | 2.49 | 0 | 0.09 | 2.81 | | | |
| LJ11-LJ12 | 4.14 | 1.97 | 0 | 0.07 | 3.56 | | | |
| LJ13-LJ14 | 3.63 | 1.72 | 0 | 0.06 | 4.06 | | | |
| LIG1d-Sa | 2.98 | 1.42 | 0.00 | 1.12 | 4.94 | 2 | 1 | 0 |
| LIG1d-S1 | 12.89 | 6.12 | 0.00 | 1.12 | 2.29 | 2 | 1 | 0 |
| LIG1d-S2 | 12.26 | 5.82 | 12.26 | 0.67 | 2.41 | 1 | 0.5 | 1 |
| LIG1d-Sb | 2.95 | 1.40 | 2.95 | 0.67 | 5.00 | 1 | 0.5 | 1 |
| LIG1d-S3 | 29.32 | 0.00 | 29.32 | 0.83 | 1.01 | 0 | 0 | 1 |

Table 7 shows the results from size exclusion-high performance liquid chromatography (SE-HPLC) analysis of the lyophilized samples shown in Table 6. Lyophilized samples were reconstituted with water and analyzed by SE-HPLC. Unprocessed NV-VLPs, analyzed concurrently, were used as a reference standard to quantify the NV-VLP content of the reconstituted test samples. Both UV and fluorescence detectors were used for quantification (data shown are from the fluorescence detector). The SE-HPLC was conducted using a Superose™ 6 10-300 column, with mobile phase consisting of 10 mM sodium phosphate, 10 mM citric acid, pH 5, and 500 mM NaCl, at a flow rate of 0.5 mL/min. Protein concentrations were quantified using integrated areas of elution peaks. "VLP" is the peak that eluted at about 15 min from the column, and any preceding shoulder and/or peak tail within the approximate elution time window of the reference standard NV-VLP analyzed concurrently. The VLP fragment that elutes from the column at around 32 min is a highly stable single species that results from destabilization and consequent disassembly of the VLP. Intermediate and smaller fragments were not observed.

The results show that combinations of sucrose and chitosan produced a wide range of native monodisperse NV-VLP recoveries including the highest (approximately 100% recovery) post-lyophilization (samples LG10-LG12). Moreover, the NV-VLP elution peak shapes from these samples were identical to the unprocessed NV-VLP reference standard indicating high preservation of native structure. Samples containing sucrose only exhibited peak shapes similar to the reference standard, though NV-VLP recoveries were lower (approx. 60% recovery (sample LG13) Samples that contained only mannitol resulted in nearly completely aggregated VLPs (samples LE1-LE6 and LIG1d-S3). The deleterious effects of mannitol on NV-VLP structure were counteracted by the presence of chitosan and sucrose (samples LIG1d-S2 and LIG1d-SB).

TABLE 7

Experiment and sample identification, and results for testing the effect of sucrose, chitosan, and mannitol or combinations thereof on stability of NV-VLP structure during freezing and lyophilization.

| Experiment and Sample | Theoretical VLP conc (mg/mL) | N | Measured SE-HPLC mean protein concentration and peak elution time | | Mean percent values of recovered protein as percent of theoretical | | Mass equivalents S = sucrose C = chitosan M = mannitol | | |
|---|---|---|---|---|---|---|---|---|---|
| | | | "VLP" ~15 min (mg/mL) | Fragment ~32 min (mg/mL) | Total protein (%) | "VLP" (%) | S | C | M |
| LE1-LE5 | 0.25 | 5 | 0.02 | 0.12 | 56.0 | 6.3 | 0 | 0 | 1 |
| LG1-LG9 | 0.25 | 9 | 0.06 | 0.00 | 24.0 | 24.0 | 0 | 1 | 0 |
| LG10 | 0.25 | 1 | 0.25 | 0.00 | 101 | 101 | 10 | 1 | 0 |
| LG11 | 0.25 | 1 | 0.25 | 0.00 | 101 | 101 | 5 | 1 | 0 |
| LG12 | 0.25 | 1 | 0.25 | 0.00 | 100 | 100 | 2.5 | 1 | 0 |
| LG13 | 0.25 | 1 | 0.16 | 0.00 | 65 | 65 | 1 | 0 | 0 |
| LJ1-LJ14 | 0.25 | 14 | 0.22 | 0 | 85.4 | 85.4 | 2 | 1 | 0 |
| LIG1d-S1 | 0.25 | 1 | 0.21 | 0 | 88 | 88 | 2 | 1 | 0 |
| LIG1d-Sa | 0.25 | 1 | 0.12 | 0 | 50 | 50 | 2 | 1 | 0 |
| LIG1d-S2 | 0.25 | 1 | 92 | 0 | 92 | 92 | 1 | 0.5 | 1 |
| LIG1d-Sb | 0.25 | 1 | 60 | 0 | 60 | 60 | 1 | 0.5 | 1 |
| LIG1d-S3 | 0.25 | 1 | <1 | <1 | <1 | <1 | 0 | 0 | 1 |

Figure 13:
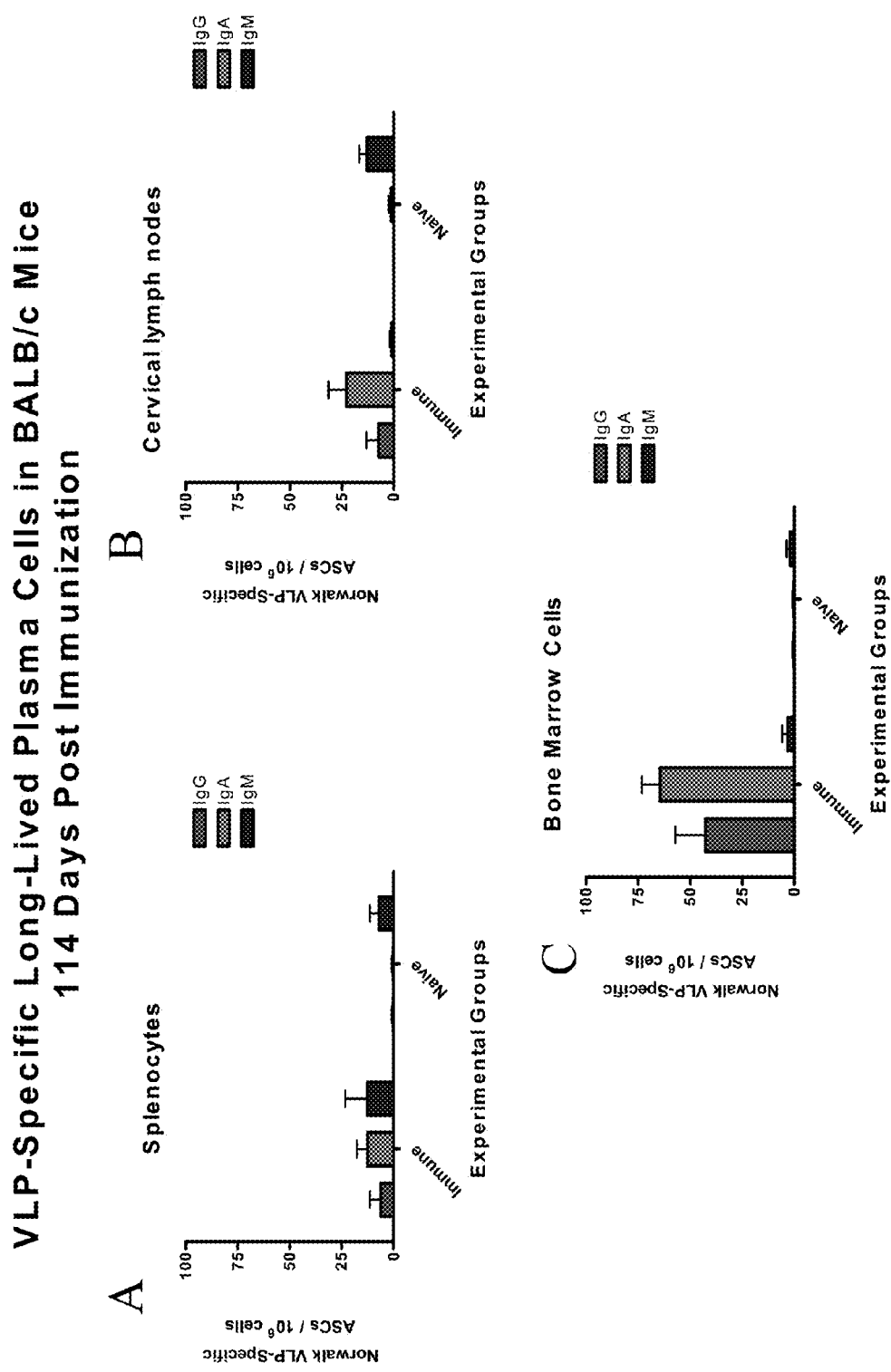
FIG. 13 shows the presence of Norwalk VLP-specific long-lived plasma cells in splenocytes (A), cervical lymph nodes (B), and bone marrow (C) in mice 114 days after intranasal immunization with Norwalk VLPs in mice.

Example 14. Induction of Norovirus-Specific Long-Lived Plasma Cells and Memory B Cells in Mice Immunized Intranasally A. Norwalk VLP-Specific Long-Lived Plasma Cells BALB/c mice were immunized intranasally with Norovirus VLPs and an adjuvant. Naïve controls were administered the adjuvant alone. At 114 days after immunization, spleen, cervical lymph nodes, and bone marrow were harvested from both groups of mice. On the day of harvesting the tissues (day 0), cells were assayed using an ELISPOT assay for the presence of antigen-specific antibody-secreting cells (ASCs). The results are presented in FIG. 13A-C for the different tissues. The detection of immunoglobulins (IgG, IgA, and IgM) in these tissues indicates the presence of Norovirus-specific long-lived plasma cells.

B. Norwalk VLP-Specific Memory B Cells

An in vitro assay was developed to detect the presence of Norwalk VLP-specific memory B-cells from mice immunized intranasally with Norwalk VLPs. Various lymphoid tissues or whole blood (peripheral blood mononuclear cells, splenocytes, lymph node cells, etc.) can serve as the source of cells that can be assayed for the presence of memory B-cells using this assay.

Figure 14:
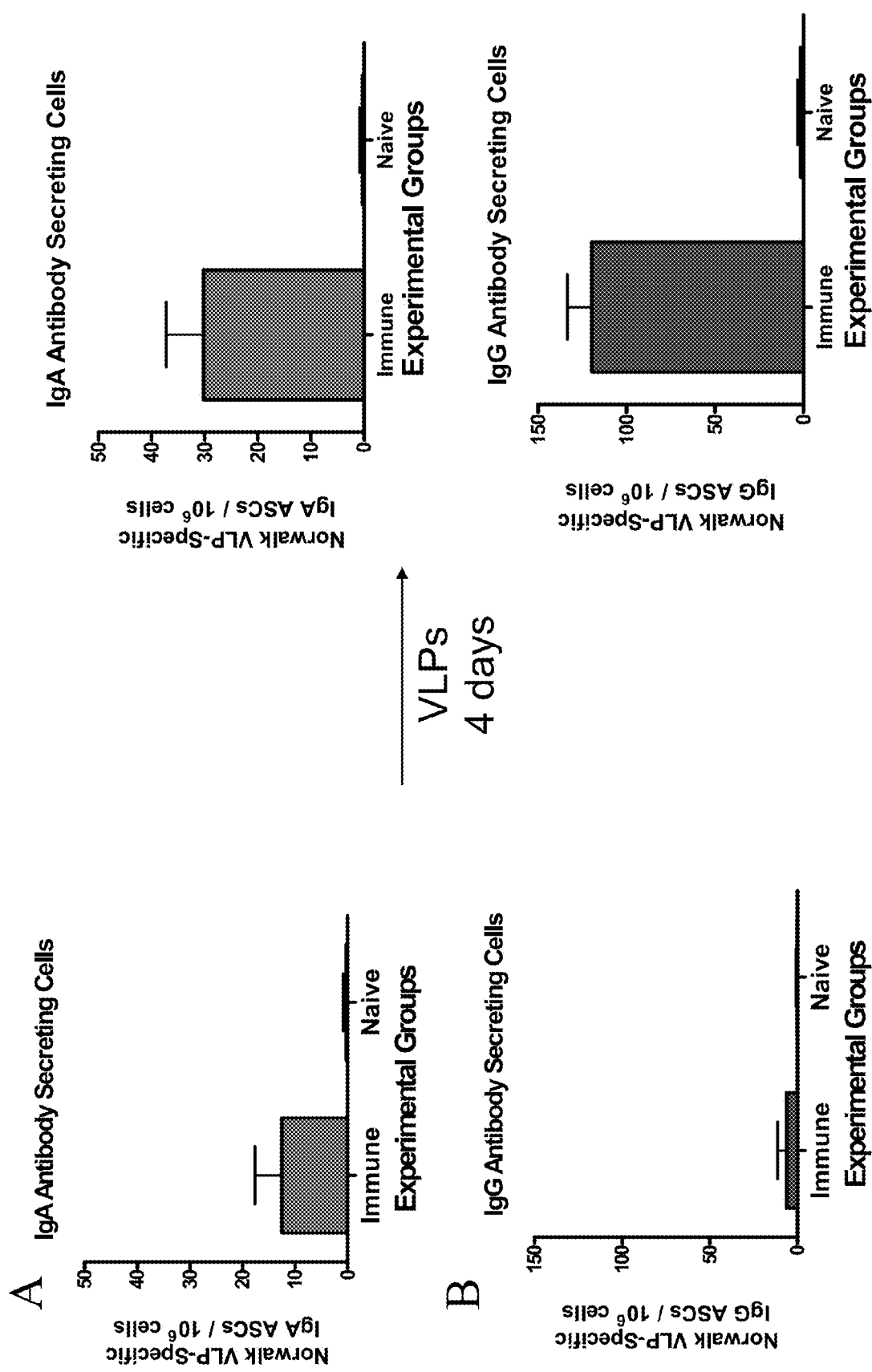
FIG. 14 depicts the Norwalk-specific memory B cell response in splenocytes of mice immunized intranasally with Norwalk VLPs. Panel A shows IgA antibody secreting cells on day 0 (left graph) and day 4 in culture with Norwalk VLPs (right graph). Panel B shows the IgG antibody secreting cells on day 0 (left graph) and day 4 in culture with Norwalk VLPs (right graph). The difference in the number of cells between day 0 and day 4 indicates the level of memory B cell expansion and differentiation.

In this experiment, the spleen was harvested and processed from immunized and naïve animals (controls), and splenocytes were cultured for four days in the presence or absence (controls) of Norwalk VLPs (20 μg/ml). An initial VLP-specific ELISPOT assay was performed on the day of tissue harvest (day 0) to establish background levels of ASCs (see Section A above). After four days in culture the cells were harvested and assayed again in an ELISPOT assay to quantify the number of VLP-specific ASCs. The difference in VLP-specific ASC numbers between the day 0 and the day 4 assays represent the antigen-specific memory B-cell population. The results of this experiment are shown in FIGS. 14A and B.

Example 15. Norovirus Memory B Cell Responses in Rabbits

Two female New Zealand White rabbits were immunized intranasally with a dry powder formulation consisting of 25 μg Norwalk VLP, 25 μg MPL, 1.5 mg mannitol, 1.5 mg sucrose, and 7.0 mg chitosan per 10 mg of dry powder loaded into Valois Mark 4 intranasal delivery devices. The two rabbits received a total of three immunizations at 14 day intervals. For these experiments, a non-immunized female rabbit was used as a naïve control.

A. Collection and Processing of Rabbit Tissues

Peripheral blood mononuclear cells (PBMCs): Whole blood (~50 mL) was obtained from rabbits in collection tubes containing EDTA to prevent coagulation. The whole blood was diluted 1:3 with sterile D-PBS and ~35 mL of diluted whole blood was layered onto 15 mL of Lympholyte Separation Medium in a sterile 50-mL centrifuge tube. The tubes were centrifuged at 800×g for 20 minutes at room temperature. The buffy coat layer containing the PBMCs was carefully removed using a sterile 5 mL pipette and the cells were washed twice with D-PBS. If necessary, contaminating red blood cells were removed by ACK lysis. The cells were resuspended in RPMI-1640-10% FBS (1640-C) and counted in a hemocytometer using a Trypan exclusion method.

Mesenteric lymph node cells: The lymph nodes were aseptically collected from each rabbit separately following euthanasia. The tissues were maintained in a sterile plastic Petri dish containing ~10 mL of RPMI-1640-No Serum (1640-NS). The lymph nodes were pressed through a sterile mesh screen using a sterile pestle to disperse the tissue and obtain a single cell suspension of lymph node cells. The cells were collected, washed twice with 1640-NS, and finally filtered through a sterile 70 μm filter to remove clumps and debris. The cells were resuspended in 1640-C and counted in a hemocytometer using a Trypan blue exclusion method.

Splenocytes: Spleens were aseptically obtained from each rabbit following euthanasia. The spleens were placed in sterile Petri dishes containing approximately 10 mL of 1640-NS. Using a sterile 22-guage needle and syringe the media was repeatedly injected into the tissue to disrupt the splenic capsule and elaborate the cells. Sterile forceps were then used to tease apart the remaining tissue fragments. The contents of the Petri dish were transferred to a sterile centrifuge tube and the cell suspension and disrupted splenic tissue was allowed to sit for 6-8 minutes to allow for the settling of large tissue fragments. The single cell suspension was transferred to a second sterile centrifuge tube and the cells were washed once with 1640-NS. The red blood cells in the splenocyte prep were removed by an ACK lysis (8 mL ACK buffer, 8 minutes, room temperature) and the cells were washed one more time with 1640-NS and finally filtered through a sterile 70 μm filter to remove clumps and debris. The final cell pellet was resuspended in 1640-Complete and counted in a hemocytometer using a Trypan blue exclusion method.

Bone marrow cells: The tibia bones in the lower legs were removed from individual rabbits following euthanasia. To remove the bone marrow cells the ends of the bones were aseptically cut off using a bone saw and the contents of the bone were flushed out by repeated injections of 1640-NS medium. The bone marrow cells were pipetted up and down repeatedly to break up and disperse clumps of cells. The cells were washed once with 1640-NS; the red blood cells were lysed with ACK, and the cells were washed one more time with 1640-NS. Finally, the cells were filtered through a sterile 70 μm filter to remove clumps and debris. The final cell pellet was resuspended in 1640-Complete and counted in a hemocytometer using a Trypan blue exclusion method.

B. ELISPOT Assays

Following pre-wetting and washing, 96-well Millipore PVDF filter plates were coated with a sterile solution of native Norwalk VLPs at a concentration of 40 μg/ml in a final volume of 50 μl/well. The plates were incubated overnight at 4° C., washed with D-PBS, and blocked with the addition of 1640-C. Mesenteric lymph node cells, splenocytes, and bone marrow cells from the immunized rabbits and from the naïve control rabbit were added to the wells at varying concentrations ($1 \times 10^6$, $5 \times 10^5$, $2 \times 10^5$, and $1 \times 10^5$ cells/well) and the plates were incubated overnight at 37° C. The plates were washed thoroughly with PBS-Tween and secondary reagents specific for rabbit IgG and IgA were added to the wells and incubated for an additional 2 hours at room temperature. Following extensive washing the plates were developed with DAB chromagen/substrate and read in an ELISPOT plate reader. Spots appearing on wells from naïve control animals were subtracted from the experimental groups. The data is expressed as Norwalk VLP-specific antibody-secreting cells (ASCs) and is normalized per $1 \times 10^6$ cells.

C. Norwalk VLP-Specific Memory B-Cell Assay

Isolated lymphoid cells from the various tissues described above were resuspended in 1640-C medium in the presence of Norwalk VLPs (10 μg/mL) at a density of $5 \times 10^6$ cells per mL. The cells were incubated in 24-well plates in 1-mL volumes for four days at 37° C. VLP-specific ELISPOT assays were performed on these cells at the time of culturing. After four days in culture the cells were harvested, washed twice with 1640-NS medium, resuspended in 1640-Complete, and counted in a hemocytometer using a Trypan blue exclusion method. The cells were tested once again in a Norwalk VLP-specific ELISPOT assay. The data obtained from the ELISPOT assays performed on the day of tissue harvest is referred to as day 0 (background) ASC activity. Any spots detected at the day 0 time point are assumed to be actively-secreting plasma cells or long-lived plasma cells (LLPCs). The data obtained from the ELISPOT assay performed on the 4-day cultured cells is referred to as day 4 ASC activity, and the memory B-cell activity is represented by the difference between day 4 ASC activity and day 0 ASC activity.

Figure 15:
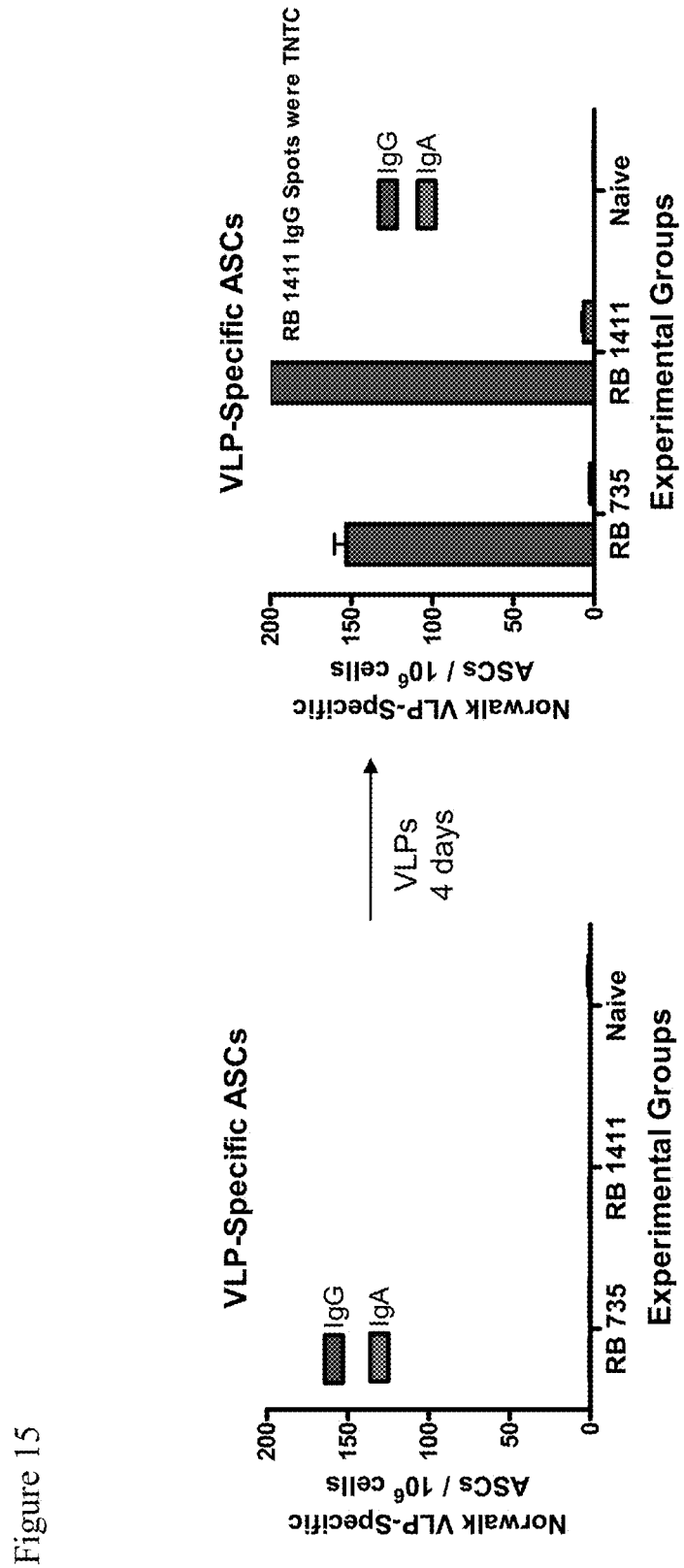
FIG. 15 shows the ELISPOT assay results of peripheral blood mononuclear cells isolated from rabbits immunized intranasally with a Norwalk VLP vaccine formulation. The left panel shows the number of Norwalk VLP-specific antigen secreting cells (ASCs) at day 0 (day of tissue harvest), while the right panel illustrates the number of Norwalk VLP-specific ASCs after 4 days in culture with Norwalk VLPs. The difference in the number of cells between day 0 and day 4 indicates the memory B cell response.

D. Norwalk VLP-Specific Memory B-Cells are Present in the Peripheral Blood of Intranasally Immunized Rabbits Whole blood was obtained from two immunized rabbits (RB735, RB1411) 141 days following the last of three intranasal immunizations with a dry powder formulation vaccine containing Norwalk VLPs as described above. Blood was also obtained from an non-immunized, naïve rabbit. The blood was processed to obtain peripheral blood mononuclear cells (PBMCs) and the PBMCs were placed in a Norwalk VLP-Specific memory B-Cell assay (section C above). The results are shown in FIG. 15. The left panel shows results of the initial ELISPOT assay at the time of tissue harvest (day 0 ASCs). The right panel shows the results of the ELISPOT assay after 4 days in culture with Norwalk VLPs (day 4 ASCs).

The day 0 ELISPOT results (FIG. 15, left panel) illustrate that there are no VLP-specific plasma cells remaining in the peripheral blood approximately 140 days after the last boost with Norwalk VLP dry powder vaccine. The right panel of FIG. 15 shows the ELISPOT assay results from PBMCs cultured for four days in vitro with Norwalk VLPs. In the two immunized rabbits, a significant number of PBMCs, presumably a subpopulation of memory B-cells, have matured into active IgG-secreting Norwalk VLP-specific plasma cells. Although assays for IgA-secreting memory B-cells were conducted, only IgG-secreting memory B-cells were detected in the PBMC population. As expected, the naïve animal showed no antigen-specific memory B-cells. Thus, VLP-specific memory B-cells were found in the peripheral circulation of rabbits 140+ days following the last of three intranasal immunizations.

Figure 16:
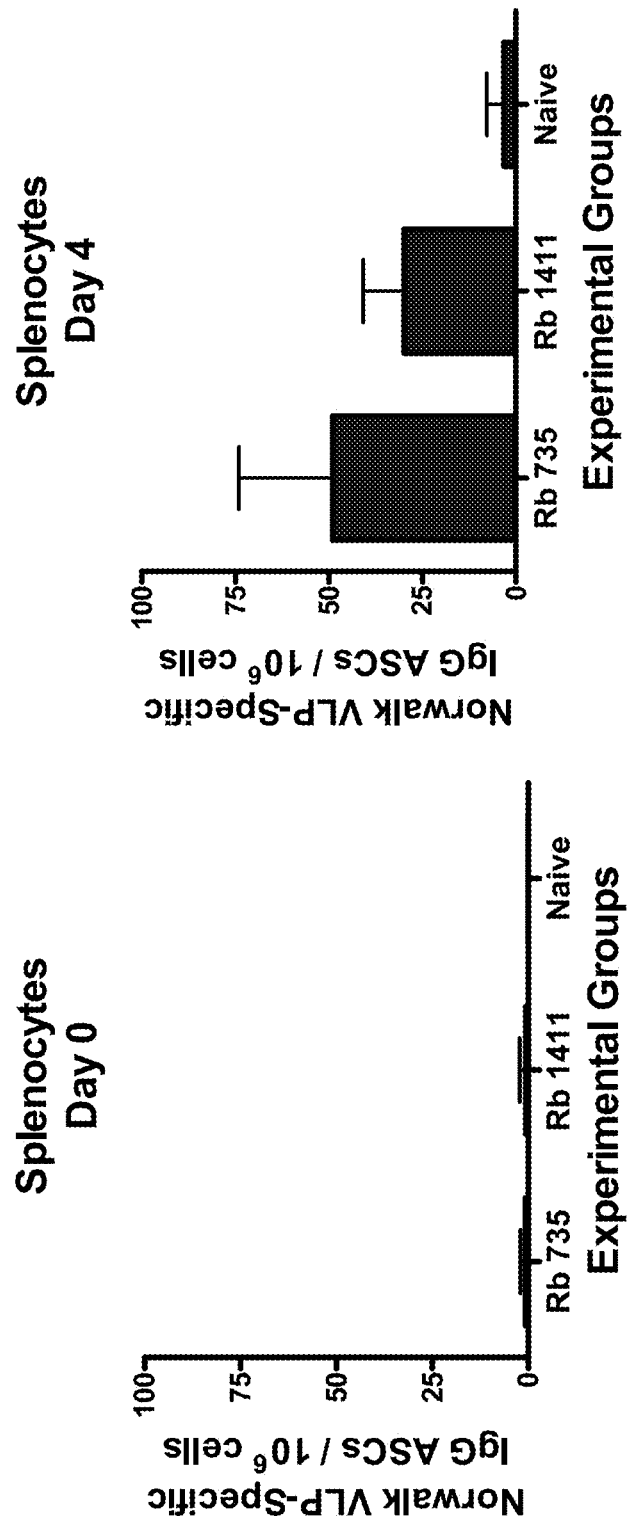
FIG. 16 shows the ELISPOT assay results of splenocytes harvested from rabbits immunized intranasally with a Norwalk VLP vaccine formulation. The left panel shows the number of Norwalk VLP-specific antigen secreting cells (ASCs) at day 0 (day of tissue harvest), while the right panel illustrates the number of Norwalk VLP-specific ASCs after 4 days in culture with Norwalk VLPs. The difference in the number of cells between day 0 and day 4 indicates the memory B cell response.

E. Norwalk VLP-Specific Memory B-Cells are Present in the Spleen of Intranasally Immunized Rabbits Splenocytes were obtained from the spleens of the two vaccine immunized rabbits and the non-immunized control rabbit. Norwalk VLP-specific memory B-cell assays (described above) were performed on these cells and the results are shown in FIG. 16. As observed for the PBMC population the day 0 ELISPOT assay shows that there are no antigen-specific plasma cells present in the spleen (FIG. 16, left panel). However, following a four day in vitro incubation with Norwalk VLPs, IgG-secreting Norwalk VLP-specific memory B-cells are apparent in the splenocyte population. Thus, the spleen represents one site for the migration of memory B-cells following intranasal immunization.

Figure 17:
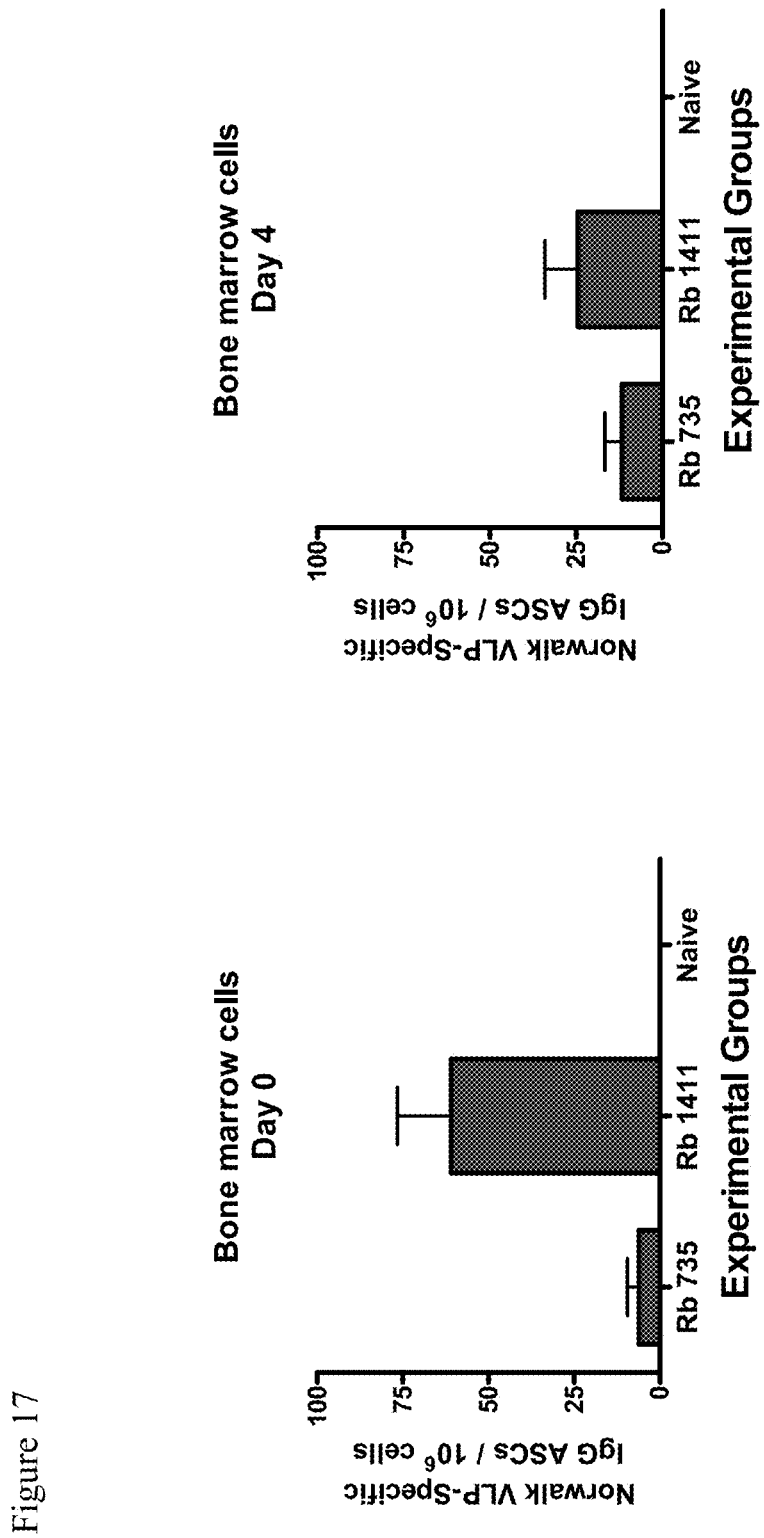
FIG. 17 shows the ELISPOT assay results of bone marrow cells harvested from the tibias of rabbits immunized intranasally with a Norwalk VLP vaccine formulation. The left panel shows the number of Norwalk VLP-specific antigen secreting cells (ASCs) at day 0 (day of tissue harvest), while the right panel illustrates the number of Norwalk VLP-specific ASCs after 4 days in culture with Norwalk VLPs. The presence of ASCs at day 0 indicates the presence of long-lived plasma cells. The difference in the number of cells between day 0 and day 4 indicates the memory B cell response.

F. A Population of Norwalk VLP-Specific Long-Lived Plasma Cells is Found in the Bone Marrow but No Memory B-Cells are Present Bone marrow cells were obtained from the tibias of the experimental rabbits and assayed for the presence of long-lived plasma cells and memory B-cells. The results are presented in FIG. 17. The left panel of FIG. 17 shows that rabbit 1411 still had a significant population of antigen-specific plasma cells in the bone marrow. Plasma cells that migrate to the bone marrow and reside there for a significant period of time following immunization are referred to as long-lived plasma cells (LLPCs). Rabbit 735 did not show a high number of LLPCs. No LLPCs were found in the bone marrow of the naïve rabbit. The bone marrow cells were cultured in a memory B-cell assay and re-tested for the presence of memory B-cells. The right panel of FIG. 17 shows that there are essentially no antigen-specific memory B-cells present in the bone marrow. Thus, long-lived plasma cells migrate to the bone marrow but no memory B-cells are found there.

Figure 18:
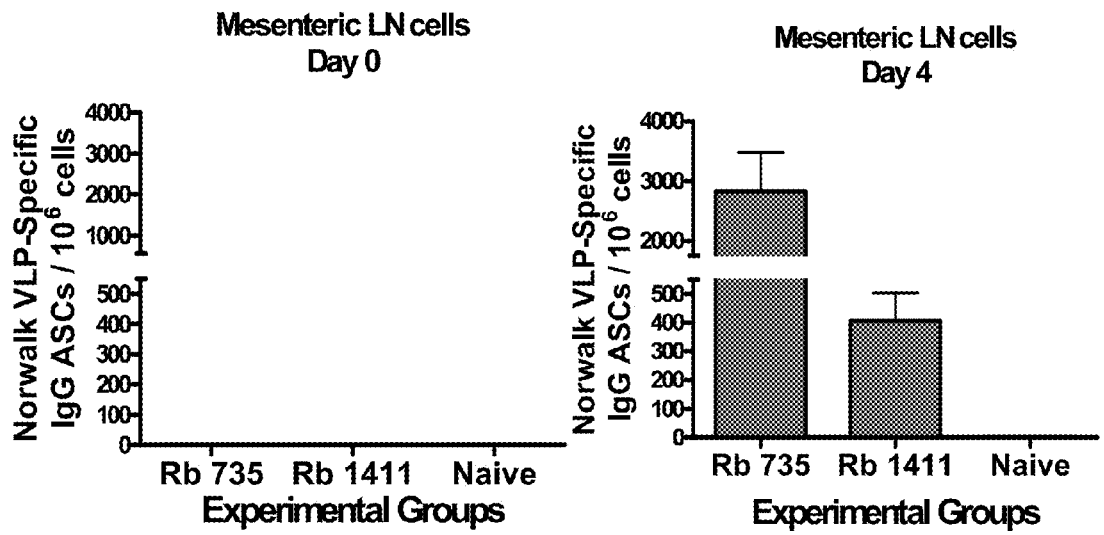
FIG. 18 shows the ELISPOT assay results of mesenteric lymph node cells harvested from rabbits immunized intranasally with a Norwalk VLP vaccine formulation. Panel A shows IgG positive antibody secreting cells (ASCs) specific for Norwalk VLPs. Panel B shows IgA positive ASCs specific for Norwalk VLPs. The left panels show the number of Norwalk VLP-specific ASCs at day 0 (day of tissue harvest), while the right panels illustrate the number of Norwalk VLP-specific ASCs after 4 days in culture with Norwalk VLPs. The presence of ASCs at day 0 indicates the presence of long-lived plasma cells. The difference in the number of cells between day 0 and day 4 indicates the memory B cell response.
Figure 18:
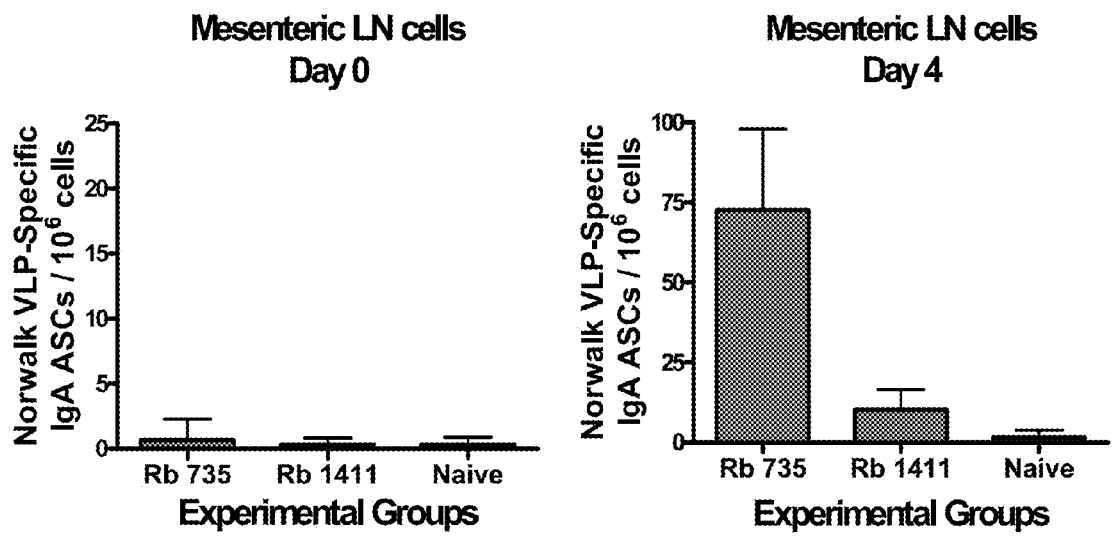

G. Both IgG-Secreting and IgA-Secreting Norwalk VLP-Specific Memory B-Cells are Present in the Mesenteric Lymph Nodes of Intranasally Immunized Rabbits The mesenteric lymph nodes were obtained from all of the experimental rabbits and the isolated cells were assayed for LLPCs and memory B-cells. The results from this assay are shown in FIG. 18A. As with most of the lymphoid tissue analyzed, except bone marrow, no LLPCs (FIG. 18A left panels) were found in the mesenteric nodes. Following in vitro incubation with Norwalk VLPs, a very high number of IgG-secreting VLP-specific memory B-cells were evident in the mesenteric lymph node population (FIG. 18A, right panel). The numbers of memory B-cells observed in the mesenteric lymph nodes were significantly higher than those observed for the other lymphoid tissues assayed.

Numerous researchers have shown that immunization at a mucosal inductive site, such as the nasal passages or the gut, is capable of eliciting a so-called mucosal immune response. This response has generally been characterized by the presence of IgA+ B-cells and IgA-secreting plasma cells localized in the mucosal lymphoid tissue. For this reason the mesenteric lymph node cells were also assayed for the presence of IgA-secreting LLPCs or memory B-cells. The results from these assays are shown in FIG. 18B. Once again, no IgA+ LLPCs were found in the mesenteric lymph node population (FIG. 18B, left panel). However, IgA-secreting memory B-cells were detected in this tissue (FIG. 18B, right panel). Thus, intranasal immunization with a dry powder Norwalk VLP vaccine formulation elicited a mucosal immune response that resulted in the migration of both IgG+ and IgA+ antigen-specific memory B-cells to the gut-associated lymphoid tissue. The production of antigen-specific memory B cells induced by immunization with the Norwalk vaccine formulation is a possible indicator of vaccine effectiveness. The presence of memory B cells is one marker of long-lasting immunity.

H. VLP-Specific CD4+ Memory T Cells

Figure 19:
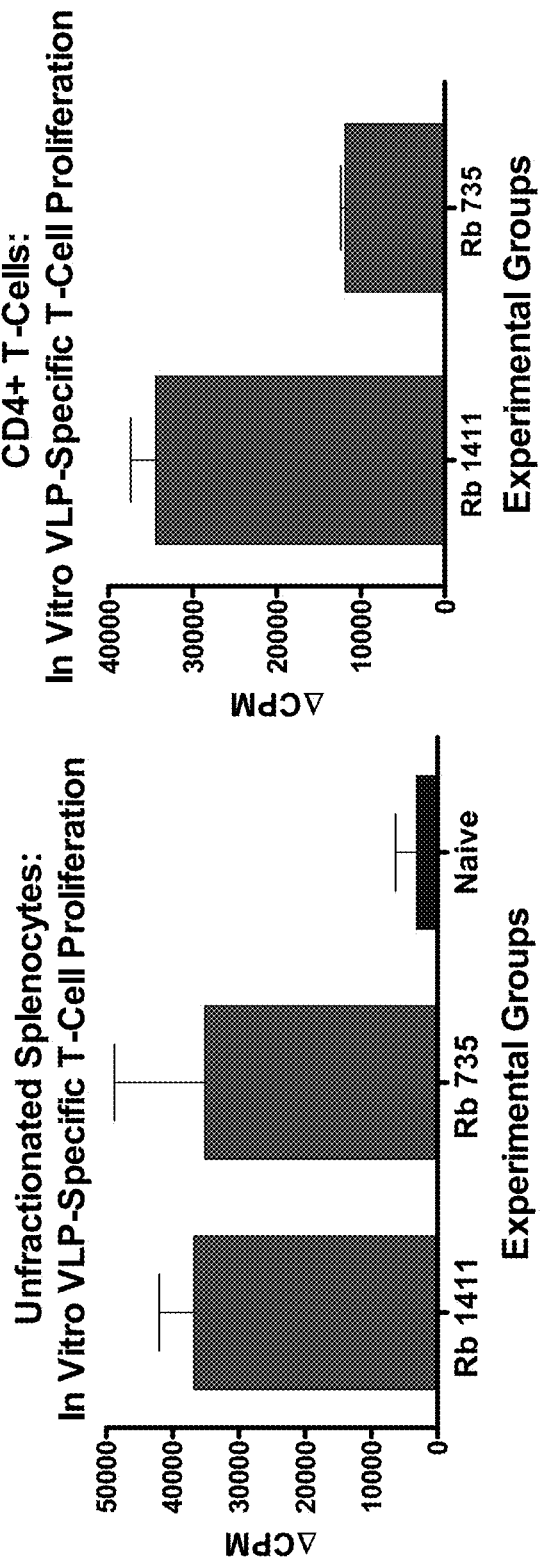
FIG. 19 illustrates in vitro antigen-specific proliferation assay of splenocytes following in vivo intranasal immunization in rabbits. The left panel shows T cell proliferation upon restimulation with Norwalk VLPs in unfractionated splenocytes, while the right panel shows CD4+ T cell proliferation upon restimulation with Norwalk VLPs.

Splenocytes harvested from immunized rabbits were restimulated with intact Norwalk VLPs and the extent of cellular proliferation was measured by tritiated thymidine incorporation as indicated on the ordinate axis (CPM) (FIG. 19). The left panel shows cellular proliferation of an unfractionated population of splenocytes, while the right panel shows cellular proliferation of CD4+ T cells.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

REFERENCES

1. Glass, R I, J S Noel, T Ando, R L Fankhauser, G Belloit, A Mounts, U D Parasher, J S Bresee and S S Monroe. The Epidemiology of Enteric Caliciviruses from Human: A Reassessment Using New Diagnostics. *J Infect Dis* 2000; 181 (Sup 2): S254-S261.
2. Hardy, M E. Norwalk and "Norwalk-like Viruses" in Epidemic Gastroenteritis. *Clin Lab Med* 1999; 19(3): 675-90.
3. Jiang, X, D Y Graham, K N Wang, and M K Estes. Noralk Virus Genome Cloning and Characterization. *Science* 1990; 250: 1580-1583.
4. Jiang, X, M Want, D Y Graham, and M K Estes. Expression, Self-Assembly, and Antigenicity of the Norwalk Virus Capsid Protein. *J Virol* 1992; 66: 6527-6532.
5. Glass, P, L J White, J M Ball, I Leparc-Goffart, M E Hardy, and M K Estes. Norwalk Virus Open Reading Frame 3 Encodes a Minor Structural Protein. *J Virol* 2000; 74: 6581-6591.
6. Lindesmith, L, C Moe, S Marionneau, N Ruvoen, X Jiang, L Lindblad, P Stewart, J LePendu, and R Baric. Human Susceptiblity and Resistance to Norwalk Virus Infection. *Nat Med* 2003; 9: 548-553.
7. Parrino, T A, D S Schreiber, J S Trier, A Z Kapikian, and N R Blacklow. Clinical Immunity in Acute Gastroenteritis Caused by Norwalk Agent. *N Engl J Med* 1977; 297: 86-89.
8. Wyatt, R G, R Dolin, N R Blacklow, H L DuPont, R F Buscho, T S Thornhill, A Z Kapikian, and R M Chanock. Comparison of Three Agents of Acute Infectious Nonbacterial Gastroenteritis by Cross-challenge in Volunteers. *J Infect Dis* 1974; 129: 709.
9. Ball, J M, D Y Graham, A R Opekum, M A Gilger, R A Guerrero, and M K Estes. Recombinant Norwalk Virus-like Particles Given Orally to Volunteers: Phase I Study. *Gastroenterology* 1999; 117: 40-48.
10. Tacket, C O, M B Sztein, G A Losonky, S S Wasserman, and M K Estes. Humoral, Mucosal, and Cellular Immune Responses to Oral Nowalk Virus-like Particles in Volunteers. *Clin Immunol* 2003; 108: 241.
11. Guerrero, R A, J M Ball, S S Krater, S E Pacheco, J D Clements, and M K Estes. Recombinant Norwalk Virus-like Particles Administered Intranasally to Mice Induce Systemic and Mucosal (Fecal and Vaginal) Immune Responses. *J Virol* 2001; 75: 9713.
12. Nicollier-Jamot, B, A Ogier, L Piroth, P Pothier, and E Kohli. Recombinant Virus-like Particles of a Norovirus (Genogroup II Strain) Administered Intranasally and Orally with Mucosal Adjuvants LT and LT (R192G) in BALB/c Mice Induce Specific Humoral and Cellular Th1/Th2-like Immune Responses. *Vaccine* 2004; 22:1079-1086.
13. Periwal, S B, K R Kourie, N Ramachandaran, S J Blakeney, S DeBruin, D Zhu, T J Zamb, L Smith, S Udem, J H Eldridge, K E Shroff, and P A Reilly. A Modified Cholera Holotoxin CT-E29H Enhances Systemic and Mucosal Immune Responses to Recombinant Norwalk Virus-like Particle Vaccine. *Vaccine* 2003; 21: 376-385.
14. Isaka, M, Y Yasuda, S Kozuka, T Taniguchi, K Matano, J Maeyama, T Komiya, K Ohkuma, N Goto, and K Tochikubo. Induction of systemic and mucosal antibody responses in mice immunized intranasally with aluminium-non-adsorbed diphtheria toxoid together with recombinant cholera toxin B subunit as an adjuvant. *Vaccine* 1999; 18: 743-751.
15. Kozlowski, P A, S Cu-Uvin, M R Neutra, and T P Flanigan. Comparison of the oral, rectal, and vaginal immunization routes for induction of antibodies in rectal and genital tract secretions of women. *Infect Immun* 1997; 65: 1387-1394.

16. Mestecky, J, S M Michalek, Z Moldoveanu, and M W Russell. Routes of immunization and antigen delivery systems for optimal mucosal immune responses in humans. *Behring Inst Mitt* 1997; 33-43.
17. Wu, H Y, and M W Russell. Nasal lymphoid tissue, intranasal immunization, and compartmentalization of the common mucosal immune system. *Immunol Res* 1997; 16: 187-201.
18. Evans, J T, C W Cluff, D A Johnson, M J Lacy, D H Persing, and J R Baldridge. Enhancement of antigen-specific immunity via the TLR4 ligands MPL adjuvant and Ribi 529. *Expert Rev Vaccines* 2003; 2: 219-229.
19. Baldridge, J R, Y Yorgensen, J R Ward, and J T Ulrich. Monophosphoryl lipid A enhances mucosal and systemic immunity to vaccine antigens following intranasal administration [In Process Citation]. *Vaccine* 2000; 18: 2416-2425.
20. Yang, Q B, M Martin, S M Michalek, and J Katz. Mechanisms of monophosphoryl lipid A augmentation of host responses to recombinant HagB from *Porphyromonas gingivalis*. *Infect Immun* 2002; 70: 3557-3565.
21. Baldrick, P, D Richardson, G Elliott, and A W Wheeler. Safety evaluation of monophosphoryl lipid A (MPL): an immunostimulatory adjuvant. *Regul Toxicol Pharmacol* 2002; 35: 398-413.
22. Baldridge, J R, P McGowan, J T Evans, C Cluff, S Mossman, D Johnson, and D Persing. Taking a toll on human disease: Toll-like receptor 4 agonists as vaccine adjuvants and monotherapeutic agents. *Expert Opin Biol Ther* 2004; 4: 1129-1138.
23. Persing, D H, R N Coler, M J Lacy, D A Johnson, J R Baldridge, R M Hershberg, and S G Reed. Taking toll: lipid A mimetics as adjuvants and immunomodulators. *Trends Microbiol* 2002; 10: S32-37.
24. Illum, L. Nasal drug delivery—possibilities, problems and solutions. *J Control Release* 2003; 87: 187-198.
25. Illum, L, I Jabbal-Gill, M Hinchcliffe, A N Fisher, and S S Davis. Chitosan as a novel nasal delivery system for vaccines. *Adv Drug Deliv Rev* 2001; 51: 81-96.
26. Davis, S S. Delivery of peptide and non-peptide drugs through the respiratory tract. *Pharm Sci Technol Today* 1999; 2: 450-456.
27. Bacon, A, J Makin, P J Sizer, I Jabbal-Gill, M Hinchcliffe, L Illum, S Chatfield, and M Roberts. Carbohydrate biopolymers enhance antibody responses to mucosally delivered vaccine antigens. *Infect Immun* 2000; 68: 5764-5770.
28. van der Lubben, I M, J C Verhoef, G Borchard, and H E Junginger. Chitosan for mucosal vaccination. *Adv Drug Deliv Rev* 2001; 52: 139-144.
29. van der Lubben, I M, J C Verhoef, G Borchard, and H E Junginger. Chitosan and its derivatives in mucosal drug and vaccine delivery. *Eur J Pharm Sci* 2001; 14: 201-207.
30. Lim, S T, B Forbes, G P Martin, and M B Brown. In vivo and in vitro characterization of novel microparticulates based on hyaluronan and chitosan hydroglutamate. *AAPS Pharm Sci Tech* 2001; 2: 20.
31. Jabbal-Gill, I, A N Fisher, R Rappuoli, S S Davis, and L Illum. Stimulation of mucosal and systemic antibody responses against *Bordetella pertussis* filamentous haemagglutinin and recombinant pertussis toxin after nasal administration with chitosan in mice. Vaccine 1998; 16: 2039-2046.
32. Mills, K H, C Cosgrove, E A McNeela, A Sexton, R Giemza, I Jabbal-Gill, A Church, W Lin, L Illum, A Podda, R Rappuoli, M Pizza, G E Griffin, and D J Lewis. Protective levels of diphtheria-neutralizing antibody induced in healthy volunteers by unilateral priming-boosting intranasal immunization associated with restricted ipsilateral mucosal secretory immunoglobulin. *A Infect Immun* 2003; 71: 726-732.
33. McNeela, E A., I Jabbal-Gill, L Illum, M Pizza, R Rappuoli, A Podda, D J Lewis, and K H Mills. Intranasal immunization with genetically detoxified diphtheria toxin induces T cell responses in humans: enhancement of Th2 responses and toxin-neutralizing antibodies by formulation with chitosan. *Vaccine* 2004; 22: 909-914.
34. Mikszta, J A., V J Sullivan, C Dean, A M Waterston, J B Alarcon, J P Dekker, 3rd, J M Brittingham, J Huang, C R Hwang, M Ferriter, G Jiang, K Mar, K U Saikh, B G Stiles, C J Roy, R G Ulrich, and N G Harvey. Protective immunization against inhalational anthrax: a comparison of minimally invasive delivery platforms. *J Infect Dis* 2005; 191: 278-288.
35. Huang, J, R J Garmise, T M Crowder, K Mar, C R Hwang, A J Hickey, J A Mikszta, and V J Sullivan. A novel dry powder influenza vaccine and intranasal delivery technology: induction of systemic and mucosal immune responses in rats. *Vaccine* 2004; 23: 794-801.
36. GSK Press Room. www.gsk.com/media/archive.htm
37. Corixa Press Room. www.corixa.com/default.asp?pid=release_detail&id=248&year=2004
38. BioMira Web Site. http://www.biomira.com/business/outLicensing/
39. Centers for Disease Control, *Morbidity and Mortality Weekly Report* 2007; 56(33):842-846.

What is claimed is:

1. A composition comprising two or more Norovirus antigens and a mucoadhesive, wherein at least one of the Norovirus antigens is from genogroup I and at least one of the Norovirus antigens is from genogroup II, and wherein the amount of each of the two or more Norovirus antigens is from about 1 µg to about 100 µg per dose.

2. The composition of claim 1, wherein the antigen comprises Norovirus virus-like particles (VLPs).

3. The composition of claim 2, wherein the Norovirus VLPs comprise a capsid protein.

4. The composition of claim 3, wherein the capsid protein is VP1 and/or VP2.

5. The composition of claim 2, wherein the VLPs are monovalent VLPs.

6. The composition of claim 2, wherein the VLPs are multivalent VLPs.

7. The composition of claim 1, wherein the genogroup I is GI.1 and the genogroup II is GII.4.

8. The composition of claim 1, wherein the mucoadhesive is selected from the group consisting of chitosan, chitosan salt, chitosan base, chitosan glutamate, polysaccharides, glycosaminoglycans, chondroitin sulfate, dermatan sulfate chondroitin, keratan sulfate, heparin, heparan sulfate, hyaluronan, pectin, alginate, glycogen, amylase, amylopectin, cellulose, chitin, stachyose, unulin, dextrin, dextran, cross-linked derivatives of poly(acrylic acid), polyvinyl alcohol, polyvinyl pyrollidone, mucin, mucopolysaccharides, cellulose derivatives, hydroxypropyl methylcellulose, carboxymethylcellulose, lectins, fimbrial proteins, and deoxyribonucleic acid.

9. The composition of claim 8, wherein the mucoadhesive is a polysaccharide.

10. The composition of claim 1, further comprising an adjuvant.

11. The composition of claim 10, wherein the adjuvant is selected from the group consisting of toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly (lactide-co-glycolides) (PLG) microparticles, poloxamer particles, microparticles, and liposomes.

12. The composition of claim 11, wherein the adjuvant is a toll-like receptor (TLR) agonist.

13. The composition of claim 12, wherein the adjuvant is MPL.

14. A method of generating antibodies to Norovirus antigens, comprising administering to a subject the composition of claim 1.

15. The method of claim 14, wherein the composition is administered to the subject by a route selected from the group consisting of mucosal, intranasal, sublingual, oral, rectal, vaginal, intramuscular, intravenous, subcutaneous, intradermal, subdermal, and transdermal routes of administration.

16. The method of claim 15, wherein the route of administration is intramuscular.

17. The method of claim 15, wherein the route of administration is intranasal.

18. The method of claim 17, wherein the composition is administered using an inhaler.

* * * * *